United States Patent
Kolb et al.

(10) Patent No.: US 8,709,015 B2
(45) Date of Patent: Apr. 29, 2014

(54) BILATERAL VERTEBRAL BODY DEROTATION SYSTEM

(75) Inventors: Eric Kolb, Sandy Hook, CT (US); James R. Donahue, East Falmouth, MA (US); Christopher Mickiewicz, Middleborough, MA (US)

(73) Assignee: Depuy Synthes Products, LLC, Raynham, MA (US)

( * ) Notice: Subject to any disclaimer, the term of this patent is extended or adjusted under 35 U.S.C. 154(b) by 1030 days.

(21) Appl. No.: 12/075,438

(22) Filed: Mar. 10, 2008

(65) Prior Publication Data

US 2009/0228051 A1    Sep. 10, 2009

(51) Int. Cl.
*A61B 17/70* (2006.01)

(52) U.S. Cl.
USPC .......................... 606/86 A; 606/246; 606/267

(58) Field of Classification Search
USPC .................................................. 606/305–308
See application file for complete search history.

(56) References Cited

U.S. PATENT DOCUMENTS

| | | |
|---|---|---|
| 410,780 A | 9/1889 | Cahn |
| 445,513 A | 1/1891 | Powell |
| 1,470,313 A | 10/1923 | Woolen |
| 1,628,144 A | 5/1927 | Herrmann |
| 1,709,766 A | 4/1929 | Bolton |
| 1,889,330 A | 11/1932 | Humes et al. |
| 1,925,385 A | 9/1933 | Humes et al. |
| 2,113,246 A | 4/1938 | Frederick |
| 2,248,054 A | 7/1941 | Becker |
| 2,248,057 A | 7/1941 | Bond |
| 2,291,413 A | 7/1942 | Siebrandt |
| 2,370,407 A | 2/1945 | Howard |
| 2,669,896 A | 2/1954 | Clough |
| 2,800,820 A | 7/1957 | Retterath |
| 2,952,285 A | 9/1960 | Roosli |
| 3,604,487 A | 9/1971 | Gilbert |
| 3,960,147 A | 6/1976 | Murray |
| 4,237,875 A | 12/1980 | Termanini |
| 4,271,836 A | 6/1981 | Bacal et al. |

(Continued)

FOREIGN PATENT DOCUMENTS

| | | |
|---|---|---|
| DE | 3923996 A1 | 1/1991 |
| DE | 4107480 A1 | 9/1992 |

(Continued)

OTHER PUBLICATIONS

Sofamor, The Spine Specialist, "Introducteur-Centreur De Tige," 7 pages. (1994).

(Continued)

*Primary Examiner* — David Isabella
*Assistant Examiner* — Suba Ganesan
(74) *Attorney, Agent, or Firm* — Nelson Mullins Riley & Scarborough LLP

(57) ABSTRACT

The disclosed embodiments provide a system including an implant assembly and an instrument configured to work in conjunction to manipulate vertebral bodies to affect derotation. The implant assemblies include a removable attachment element that allows for the attachment of the instrument. The instrument is configured to attach to two implant assemblies that have been inserted bilaterally into a vertebral body. When the instrument is attached to the implant assemblies, forces applied to the instrument are translated and transferred to the implant assemblies and the vertebral body into which the implant assemblies have been inserted thereby providing a rotational force on the vertebral body.

7 Claims, 18 Drawing Sheets

(56) References Cited

U.S. PATENT DOCUMENTS

| | | |
|---|---|---|
| 4,363,250 A | 12/1982 | Suga |
| 4,411,259 A | 10/1983 | Drummond |
| 4,445,513 A | 5/1984 | Ulrich et al. |
| 4,655,223 A | 4/1987 | Kim |
| 4,733,657 A | 3/1988 | Kluger |
| 4,743,260 A | 5/1988 | Burton |
| 4,809,695 A | 3/1989 | Gwathmey et al. |
| 4,887,596 A | 12/1989 | Sherman |
| 4,896,661 A | 1/1990 | Bogert et al. |
| 4,957,495 A | 9/1990 | Kluger et al. |
| 4,987,892 A | 1/1991 | Krag et al. |
| 5,005,562 A | 4/1991 | Cotrel |
| 5,014,407 A | 5/1991 | Boughten et al. |
| 5,020,519 A | 6/1991 | Hayes et al. |
| 5,067,955 A | 11/1991 | Cotrel |
| 5,092,866 A | 3/1992 | Breard et al. |
| 5,120,171 A | 6/1992 | Lasner |
| 5,176,678 A | 1/1993 | Tsou |
| 5,176,680 A | 1/1993 | Vignaud et al. |
| 5,181,917 A | 1/1993 | Rogozinski |
| 5,181,971 A | 1/1993 | Ohtsuka |
| 5,190,543 A | 3/1993 | Schlapfer |
| 5,219,349 A | 6/1993 | Krag et al. |
| 5,226,766 A | 7/1993 | Lasner |
| 5,263,939 A | 11/1993 | Wortrich |
| 5,282,801 A | 2/1994 | Sherman |
| 5,282,863 A | 2/1994 | Burton |
| D346,217 S | 4/1994 | Sparker et al. |
| 5,306,248 A | 4/1994 | Barrington |
| 5,330,474 A | 7/1994 | Lin |
| 5,360,431 A | 11/1994 | Puno et al. |
| 5,364,397 A | 11/1994 | Hayes et al. |
| 5,385,565 A | 1/1995 | Ray |
| 5,387,213 A | 2/1995 | Breard et al. |
| 5,391,170 A | 2/1995 | McGuire et al. |
| 5,415,661 A | 5/1995 | Holmes |
| 5,429,641 A | 7/1995 | Gotfried |
| 5,468,241 A | 11/1995 | Metz-Stavenhagen et al. |
| 5,478,340 A | 12/1995 | Kluger |
| 5,484,440 A | 1/1996 | Allard |
| 5,487,744 A | 1/1996 | Howland |
| 5,499,983 A | 3/1996 | Hughes |
| 5,501,684 A | 3/1996 | Schlapfer et al. |
| 5,520,689 A | 5/1996 | Schlapfer et al. |
| 5,536,127 A | 7/1996 | Pennig |
| 5,536,268 A | 7/1996 | Griss |
| 5,540,688 A | 7/1996 | Navas |
| 5,545,165 A | 8/1996 | Biedermann et al. |
| 5,549,608 A | 8/1996 | Errico et al. |
| 5,551,320 A | 9/1996 | Horobec et al. |
| 5,591,166 A | 1/1997 | Bernhardt et al. |
| 5,616,143 A | 4/1997 | Schlapfer et al. |
| 5,649,931 A | 7/1997 | Bryant et al. |
| 5,667,513 A | 9/1997 | Torrie et al. |
| 5,672,175 A | 9/1997 | Martin |
| 5,672,176 A | 9/1997 | Biedermann et al. |
| 5,683,399 A | 11/1997 | Jones |
| 5,697,933 A | 12/1997 | Gundlapalli et al. |
| 5,707,371 A | 1/1998 | Metz-Stavenhagen |
| 5,720,751 A | 2/1998 | Jackson |
| 5,725,532 A | 3/1998 | Shoemaker |
| 5,746,757 A | 5/1998 | McGuire |
| 5,782,831 A | 7/1998 | Sherman et al. |
| 5,797,910 A | 8/1998 | Martin |
| 5,797,911 A | 8/1998 | Sherman et al. |
| 5,810,878 A | 9/1998 | Burel et al. |
| 5,814,046 A | 9/1998 | Hopf |
| 5,879,350 A | 3/1999 | Sherman et al. |
| 5,882,350 A | 3/1999 | Ralph et al. |
| 5,885,285 A | 3/1999 | Simonson |
| RE36,211 E | 5/1999 | Nonomura |
| RE36,221 E | 6/1999 | Breard et al. |
| 5,910,141 A | 6/1999 | Morrison et al. |
| 5,941,885 A | 8/1999 | Jackson |
| 5,951,555 A | 9/1999 | Rehak et al. |
| 5,951,564 A | 9/1999 | Schroder et al. |
| 5,951,579 A | 9/1999 | Dykes |
| 5,964,760 A | 10/1999 | Richelsoph |
| 5,976,133 A | 11/1999 | Kraus et al. |
| 5,989,250 A | 11/1999 | Wagner et al. |
| 5,989,254 A | 11/1999 | Katz |
| 6,010,509 A | 1/2000 | Delgado et al. |
| 6,036,692 A | 3/2000 | Burel et al. |
| 6,050,997 A | 4/2000 | Mullane |
| 6,063,090 A | 5/2000 | Schlapfer |
| 6,074,391 A | 6/2000 | Metz-Stavenhagen et al. |
| 6,090,110 A | 7/2000 | Metz-Stavenhagen |
| 6,090,113 A | 7/2000 | Le Couedic et al. |
| 6,099,528 A | 8/2000 | Saurat |
| 6,123,707 A | 9/2000 | Wagner |
| 6,139,549 A | 10/2000 | Keller |
| 6,146,383 A | 11/2000 | Studer et al. |
| 6,183,472 B1 | 2/2001 | Lutz |
| 6,189,422 B1 | 2/2001 | Stihl |
| 6,204,060 B1 | 3/2001 | Mehtali et al. |
| 6,210,330 B1 | 4/2001 | Tepper |
| 6,235,028 B1 | 5/2001 | Brumfield et al. |
| 6,251,112 B1 | 6/2001 | Jackson |
| 6,254,602 B1 | 7/2001 | Justis |
| 6,258,090 B1 | 7/2001 | Jackson |
| 6,261,287 B1 | 7/2001 | Metz-Stavenhagen |
| 6,280,442 B1 | 8/2001 | Barker et al. |
| 6,280,443 B1 | 8/2001 | Gu et al. |
| 6,299,616 B1 | 10/2001 | Beger |
| 6,302,888 B1 | 10/2001 | Mellinger et al. |
| 6,309,389 B1 | 10/2001 | Baccelli |
| 6,368,321 B1 | 4/2002 | Jackson |
| 6,371,973 B1 | 4/2002 | Tepper |
| 6,379,357 B1 | 4/2002 | Bernstein et al. |
| 6,423,065 B2 | 7/2002 | Ferree |
| 6,440,133 B1 | 8/2002 | Beale et al. |
| 6,440,137 B1 | 8/2002 | Horvath et al. |
| 6,440,142 B1 | 8/2002 | Ralph et al. |
| 6,440,144 B1 | 8/2002 | Bacher |
| 6,443,953 B1 | 9/2002 | Perra et al. |
| 6,478,798 B1 | 11/2002 | Howland |
| 6,511,484 B2 | 1/2003 | Torode et al. |
| 6,530,929 B1 | 3/2003 | Justis et al. |
| 6,540,748 B2 | 4/2003 | Lombardo |
| 6,565,567 B1 | 5/2003 | Haider |
| 6,589,249 B2 | 7/2003 | Sater et al. |
| 6,597,279 B1 | 7/2003 | Haraguchi |
| 6,623,485 B2 | 9/2003 | Doubler et al. |
| 6,648,888 B1 | 11/2003 | Shluzas |
| 6,652,523 B1 | 11/2003 | Evrard et al. |
| 6,660,006 B2 | 12/2003 | Markworth et al. |
| 6,689,137 B2 | 2/2004 | Reed |
| 6,692,500 B2 | 2/2004 | Reed |
| 6,695,843 B2 | 2/2004 | Biedermann et al. |
| 6,716,214 B1 | 4/2004 | Jackson |
| 6,726,692 B2 | 4/2004 | Bette et al. |
| 6,733,502 B2 | 5/2004 | Altarac et al. |
| 6,743,231 B1 | 6/2004 | Gray et al. |
| 6,746,449 B2 | 6/2004 | Jones et al. |
| 6,749,613 B1 | 6/2004 | Conchy et al. |
| 6,752,832 B2 | 6/2004 | Neumann |
| 6,755,829 B1 | 6/2004 | Bono et al. |
| 6,783,527 B2 | 8/2004 | Drewry et al. |
| 6,790,208 B2 | 9/2004 | Oribe et al. |
| 6,790,209 B2 | 9/2004 | Beale et al. |
| 6,800,078 B2 | 10/2004 | Reed |
| 6,800,079 B2 | 10/2004 | Reed |
| 6,827,722 B1 | 12/2004 | Schoenefeld |
| 6,837,889 B2 | 1/2005 | Shluzas |
| 6,964,666 B2 | 11/2005 | Jackson |
| 7,083,621 B2 | 8/2006 | Shaolian et al. |
| 7,156,849 B2 | 1/2007 | Dunbar et al. |
| 7,160,300 B2 | 1/2007 | Jackson |
| 7,179,254 B2 | 2/2007 | Pendekanti et al. |
| 7,179,261 B2 | 2/2007 | Sicvol et al. |
| 7,250,052 B2 | 7/2007 | Landry et al. |
| 7,278,995 B2 | 10/2007 | Nichols et al. |
| 7,320,689 B2 | 1/2008 | Keller |
| 7,322,979 B2 | 1/2008 | Crandall et al. |

(56) References Cited

U.S. PATENT DOCUMENTS

| | | | |
|---|---|---|---|
| 7,371,239 B2 | 5/2008 | Dec et al. | |
| 7,455,685 B2 | 11/2008 | Justis | |
| 7,462,182 B2 | 12/2008 | Lim | |
| 7,465,306 B2 | 12/2008 | Pond, Jr. et al. | |
| 7,470,279 B2 | 12/2008 | Jackson | |
| 7,485,120 B2 | 2/2009 | Ray | |
| 7,491,207 B2 | 2/2009 | Keyer et al. | |
| 7,491,208 B2 | 2/2009 | Pond, Jr. et al. | |
| 7,491,218 B2 * | 2/2009 | Landry et al. | 606/246 |
| 7,527,638 B2 | 5/2009 | Anderson et al. | |
| 7,572,281 B2 | 8/2009 | Runco et al. | |
| 7,588,585 B2 | 9/2009 | Gold et al. | |
| 7,591,836 B2 | 9/2009 | Dick et al. | |
| 7,621,918 B2 | 11/2009 | Jackson | |
| 7,651,502 B2 | 1/2010 | Jackson | |
| 7,666,188 B2 | 2/2010 | Anderson et al. | |
| 7,666,189 B2 | 2/2010 | Gerber et al. | |
| 7,708,736 B2 | 5/2010 | Mullaney | |
| 7,708,763 B2 | 5/2010 | Selover et al. | |
| 7,766,944 B2 | 8/2010 | Metz-Stavenhagen | |
| 7,794,464 B2 * | 9/2010 | Bridwell et al. | 606/86 A |
| 7,867,237 B2 | 1/2011 | Stad et al. | |
| 7,887,539 B2 | 2/2011 | Dunbar, Jr. et al. | |
| 7,887,541 B2 | 2/2011 | Runco et al. | |
| 7,951,168 B2 | 5/2011 | Chao et al. | |
| 7,951,172 B2 | 5/2011 | Chao et al. | |
| 7,951,175 B2 | 5/2011 | Chao et al. | |
| 7,988,698 B2 | 8/2011 | Rosenberg et al. | |
| 8,007,516 B2 | 8/2011 | Chao et al. | |
| 8,172,847 B2 | 5/2012 | Dziedzic et al. | |
| 2001/0020169 A1 | 9/2001 | Metz-Stavenhagen | |
| 2001/0029376 A1 | 10/2001 | Sater et al. | |
| 2002/0035366 A1 | 3/2002 | Walder et al. | |
| 2002/0082599 A1 | 6/2002 | Crandall et al. | |
| 2002/0095153 A1 | 7/2002 | Jones et al. | |
| 2002/0133155 A1 | 9/2002 | Ferree | |
| 2002/0143341 A1 | 10/2002 | Biedermann et al. | |
| 2002/0173789 A1 | 11/2002 | Howland | |
| 2003/0009168 A1 | 1/2003 | Beale et al. | |
| 2003/0028195 A1 | 2/2003 | Bette | |
| 2003/0073995 A1 | 4/2003 | Reed | |
| 2003/0083657 A1 | 5/2003 | Drewry et al. | |
| 2003/0083747 A1 | 5/2003 | Winterbottom et al. | |
| 2003/0088248 A1 | 5/2003 | Reed | |
| 2003/0100896 A1 | 5/2003 | Biedermann et al. | |
| 2003/0105460 A1 | 6/2003 | Crandall et al. | |
| 2003/0109880 A1 | 6/2003 | Shirado et al. | |
| 2003/0114852 A1 | 6/2003 | Biedermann et al. | |
| 2003/0125750 A1 | 7/2003 | Zwirnmann et al. | |
| 2003/0149438 A1 | 8/2003 | Nichols et al. | |
| 2003/0171749 A1 | 9/2003 | Le Couedic et al. | |
| 2003/0176861 A1 | 9/2003 | Reed | |
| 2003/0191370 A1 | 10/2003 | Phillips | |
| 2003/0191470 A1 | 10/2003 | Ritland | |
| 2003/0199872 A1 | 10/2003 | Markworth et al. | |
| 2003/0203488 A1 | 10/2003 | Mehtali et al. | |
| 2003/0220642 A1 | 11/2003 | Freudiger | |
| 2003/0220643 A1 | 11/2003 | Ferree | |
| 2003/0225408 A1 | 12/2003 | Nichols et al. | |
| 2004/0002708 A1 | 1/2004 | Ritland | |
| 2004/0036254 A1 | 2/2004 | Patton | |
| 2004/0049189 A1 | 3/2004 | Le Couedic et al. | |
| 2004/0049190 A1 | 3/2004 | Biedermann et al. | |
| 2004/0049191 A1 | 3/2004 | Markworth et al. | |
| 2004/0073215 A1 | 4/2004 | Carli | |
| 2004/0102789 A1 | 5/2004 | Baughman | |
| 2004/0147936 A1 | 7/2004 | Rosenberg et al. | |
| 2004/0147937 A1 | 7/2004 | Dunbar et al. | |
| 2004/0158257 A1 | 8/2004 | Bonati et al. | |
| 2004/0158258 A1 | 8/2004 | Bonati et al. | |
| 2004/0172025 A1 | 9/2004 | Drewry et al. | |
| 2004/0172057 A1 | 9/2004 | Guillebon et al. | |
| 2004/0176779 A1 | 9/2004 | Casutt et al. | |
| 2004/0181224 A1 | 9/2004 | Biedermann et al. | |
| 2004/0186473 A1 | 9/2004 | Cournoyer et al. | |
| 2004/0204711 A1 | 10/2004 | Jackson | |
| 2004/0220567 A1 | 11/2004 | Eisermann et al. | |
| 2004/0225289 A1 | 11/2004 | Biedermann et al. | |
| 2004/0243139 A1 | 12/2004 | Lewis et al. | |
| 2004/0254576 A1 | 12/2004 | Dunbar, Jr. et al. | |
| 2004/0267260 A1 | 12/2004 | Mack et al. | |
| 2004/0267275 A1 | 12/2004 | Cournoyer et al. | |
| 2005/0015095 A1 | 1/2005 | Keller | |
| 2005/0033291 A1 | 2/2005 | Ebara | |
| 2005/0033295 A1 | 2/2005 | Wisnewski | |
| 2005/0033299 A1 | 2/2005 | Shluzas | |
| 2005/0055031 A1 | 3/2005 | Lim | |
| 2005/0059969 A1 | 3/2005 | McKinley | |
| 2005/0065514 A1 | 3/2005 | Studer | |
| 2005/0065515 A1 | 3/2005 | Jahng | |
| 2005/0065516 A1 | 3/2005 | Jahng | |
| 2005/0065517 A1 | 3/2005 | Chin | |
| 2005/0070917 A1 | 3/2005 | Justis | |
| 2005/0079909 A1 | 4/2005 | Singhaseni | |
| 2005/0085813 A1 | 4/2005 | Spitler et al. | |
| 2005/0085815 A1 | 4/2005 | Harms et al. | |
| 2005/0090824 A1 | 4/2005 | Shluzas et al. | |
| 2005/0131408 A1 * | 6/2005 | Sicvol et al. | 606/61 |
| 2005/0131420 A1 | 6/2005 | Techiera et al. | |
| 2005/0131421 A1 | 6/2005 | Anderson et al. | |
| 2005/0131422 A1 | 6/2005 | Anderson et al. | |
| 2005/0137593 A1 | 6/2005 | Gray et al. | |
| 2005/0143749 A1 | 6/2005 | Zalenski et al. | |
| 2005/0149036 A1 | 7/2005 | Varieur et al. | |
| 2005/0149048 A1 | 7/2005 | Leport et al. | |
| 2005/0149053 A1 | 7/2005 | Varieur et al. | |
| 2005/0154389 A1 | 7/2005 | Selover et al. | |
| 2005/0159650 A1 | 7/2005 | Raymond et al. | |
| 2005/0177163 A1 | 8/2005 | Abdou | |
| 2005/0192570 A1 | 9/2005 | Jackson | |
| 2005/0192573 A1 | 9/2005 | Abdelgany et al. | |
| 2005/0192579 A1 | 9/2005 | Jackson | |
| 2005/0192589 A1 | 9/2005 | Raymond et al. | |
| 2005/0222570 A1 | 10/2005 | Jackson | |
| 2005/0228376 A1 | 10/2005 | Boomer et al. | |
| 2005/0228380 A1 | 10/2005 | Moore et al. | |
| 2005/0228392 A1 | 10/2005 | Keyer et al. | |
| 2005/0228400 A1 | 10/2005 | Chao et al. | |
| 2005/0234449 A1 | 10/2005 | Aferzon | |
| 2005/0245928 A1 | 11/2005 | Colleran et al. | |
| 2005/0261687 A1 | 11/2005 | Garamszegi et al. | |
| 2005/0261702 A1 | 11/2005 | Oribe et al. | |
| 2005/0283244 A1 | 12/2005 | Gordon et al. | |
| 2005/0288668 A1 | 12/2005 | Brinkhaus | |
| 2006/0009775 A1 | 1/2006 | Dec et al. | |
| 2006/0025768 A1 | 2/2006 | Iott et al. | |
| 2006/0036254 A1 | 2/2006 | Lim | |
| 2006/0036255 A1 | 2/2006 | Pond et al. | |
| 2006/0036260 A1 | 2/2006 | Runco et al. | |
| 2006/0069391 A1 | 3/2006 | Jackson | |
| 2006/0074418 A1 | 4/2006 | Jackson | |
| 2006/0079909 A1 | 4/2006 | Runco et al. | |
| 2006/0089651 A1 | 4/2006 | Trudeau et al. | |
| 2006/0095035 A1 | 5/2006 | Jones et al. | |
| 2006/0111712 A1 | 5/2006 | Jackson | |
| 2006/0111713 A1 | 5/2006 | Jackson | |
| 2006/0111730 A1 | 5/2006 | Hay | |
| 2006/0149236 A1 | 7/2006 | Barry | |
| 2006/0155277 A1 | 7/2006 | Metz-Stavenhagen | |
| 2006/0166534 A1 | 7/2006 | Brumfield et al. | |
| 2006/0166535 A1 | 7/2006 | Brumfield et al. | |
| 2006/0173454 A1 | 8/2006 | Spitler et al. | |
| 2006/0195092 A1 | 8/2006 | Barry | |
| 2006/0200131 A1 | 9/2006 | Chao et al. | |
| 2006/0200132 A1 | 9/2006 | Chao et al. | |
| 2006/0217735 A1 | 9/2006 | MacDonald et al. | |
| 2006/0229605 A1 | 10/2006 | Olsen | |
| 2006/0229614 A1 | 10/2006 | Foley et al. | |
| 2006/0247630 A1 | 11/2006 | Iott et al. | |
| 2006/0264934 A1 | 11/2006 | Fallin | |
| 2006/0271050 A1 | 11/2006 | Piza Vallespir | |
| 2006/0282073 A1 | 12/2006 | Simanovsky | |
| 2006/0293690 A1 | 12/2006 | Abdelgany | |
| 2006/0293692 A1 | 12/2006 | Whipple et al. | |

(56) References Cited

U.S. PATENT DOCUMENTS

| | | |
|---|---|---|
| 2007/0078460 A1 | 4/2007 | Frigg et al. |
| 2007/0093849 A1 | 4/2007 | Jones et al. |
| 2007/0129731 A1 | 6/2007 | Sicvol et al. |
| 2007/0162009 A1 | 7/2007 | Chao et al. |
| 2007/0162010 A1 | 7/2007 | Chao et al. |
| 2007/0167954 A1 | 7/2007 | Sicvol et al. |
| 2007/0173831 A1 | 7/2007 | Abdou |
| 2007/0185375 A1 | 8/2007 | Stad et al. |
| 2007/0191836 A1 | 8/2007 | Justis |
| 2007/0213715 A1 | 9/2007 | Bridwell et al. |
| 2007/0213716 A1 | 9/2007 | Lenke et al. |
| 2007/0213722 A1 | 9/2007 | Jones et al. |
| 2007/0231059 A1 | 10/2007 | Mullaney |
| 2007/0233079 A1 | 10/2007 | Fallin et al. |
| 2007/0233097 A1 | 10/2007 | Anderson et al. |
| 2007/0260261 A1 | 11/2007 | Runco et al. |
| 2007/0270880 A1 | 11/2007 | Lindemann et al. |
| 2008/0045956 A1 | 2/2008 | Songer et al. |
| 2008/0077134 A1 | 3/2008 | Dziedzic et al. |
| 2008/0077135 A1 | 3/2008 | Stad et al. |
| 2008/0172062 A1 | 7/2008 | Donahue et al. |
| 2008/0195159 A1 | 8/2008 | Kloss et al. |
| 2008/0243190 A1 | 10/2008 | Dziedzic et al. |
| 2008/0255574 A1 | 10/2008 | Dye |
| 2008/0288005 A1 | 11/2008 | Jackson |
| 2009/0018541 A1 | 1/2009 | Lavi |
| 2009/0030419 A1 | 1/2009 | Runco et al. |
| 2009/0030420 A1 | 1/2009 | Runco et al. |
| 2009/0054902 A1 | 2/2009 | Mickiewicz et al. |
| 2009/0062857 A1 | 3/2009 | Ramsay et al. |
| 2009/0082811 A1 | 3/2009 | Stad et al. |
| 2009/0088764 A1 | 4/2009 | Stad et al. |
| 2009/0138056 A1 | 5/2009 | Anderson et al. |
| 2009/0143828 A1 | 6/2009 | Stad et al. |
| 2009/0228051 A1 | 9/2009 | Kolb et al. |
| 2009/0228053 A1 | 9/2009 | Kolb et al. |
| 2010/0137915 A1 | 6/2010 | Anderson et al. |
| 2011/0034961 A1 | 2/2011 | Runco et al. |
| 2011/0034962 A1 | 2/2011 | Dunbar, Jr. et al. |
| 2011/0077689 A1 | 3/2011 | Mickiewicz et al. |
| 2011/0144695 A1 | 6/2011 | Rosenberg et al. |
| 2011/0282402 A1 | 11/2011 | Chao et al. |

FOREIGN PATENT DOCUMENTS

| | | |
|---|---|---|
| DE | 4238339 A1 | 5/1994 |
| DE | 29806563 U1 | 7/1998 |
| DE | 10005385 A1 | 8/2001 |
| DE | 10005386 A1 | 8/2001 |
| DE | 20207851 U1 | 11/2002 |
| EP | 0328883 A2 | 8/1989 |
| EP | 0381588 B2 | 8/1990 |
| EP | 0441729 B1 | 8/1991 |
| EP | 0487895 A1 | 6/1992 |
| EP | 0572790 B1 | 12/1993 |
| EP | 0592266 A1 | 4/1994 |
| EP | 0669109 B1 | 8/1995 |
| EP | 0558883 B1 | 7/1997 |
| EP | 0784693 A1 | 7/1997 |
| EP | 0880344 B1 | 12/1998 |
| EP | 0885598 A2 | 12/1998 |
| EP | 0948939 A1 | 10/1999 |
| EP | 0951246 B1 | 10/1999 |
| EP | 1023873 A2 | 8/2000 |
| EP | 1090595 A2 | 4/2001 |
| EP | 1295566 A1 | 3/2003 |
| EP | 1364622 B1 | 11/2003 |
| EP | 1574175 A1 | 9/2005 |
| FR | 2677242 A1 | 12/1992 |
| FR | 2680314 A1 | 2/1993 |
| FR | 2729291 A1 | 7/1996 |
| JP | 2003-52708 | 2/2003 |
| JP | 2007-525274 | 9/2007 |
| WO | 90/02527 A1 | 3/1990 |
| WO | 96/21396 A1 | 7/1996 |
| WO | 98/22033 A1 | 5/1998 |
| WO | 98/25534 A1 | 6/1998 |
| WO | 99/44527 A1 | 9/1999 |
| WO | 01/45576 A1 | 6/2001 |
| WO | 02/07622 A1 | 1/2002 |
| WO | 02/102259 A2 | 12/2002 |
| WO | 03/007828 A1 | 1/2003 |
| WO | 03/032863 A2 | 4/2003 |
| WO | 03/049629 A1 | 6/2003 |
| WO | 2004/019755 A2 | 3/2004 |
| WO | 2004/034916 A1 | 4/2004 |
| WO | 2005/006948 A2 | 1/2005 |
| WO | 2005/013839 A2 | 2/2005 |
| WO | 2005/030065 A1 | 4/2005 |
| WO | 2005/044117 A2 | 5/2005 |
| WO | 2005/044123 A1 | 5/2005 |
| WO | 2005/072081 A2 | 8/2005 |
| WO | 2006/020443 A1 | 2/2006 |
| WO | 2007/092797 A2 | 8/2007 |
| WO | 2007/092870 A2 | 8/2007 |
| WO | 2007/092876 A2 | 8/2007 |
| WO | 2007/149426 A2 | 12/2007 |
| WO | 2008/024937 A2 | 2/2008 |

OTHER PUBLICATIONS

Wiltse, Leon L. et al., "History of Pedicle Screw Fixation of the Spine," Spine, State of the Art Reviews, vol. 6(1):1-10 (1992).
Canadian Office Action for Application No. 2,717,758, 2 pages, dated May 4, 2012.
Chinese Office Action for Application No. 200980116856.2, 10 pages, dated Apr. 18, 2012.
European Office Action for Application No. 06736870, dated Dec. 18, 2009.
European Office Action for Application No. 06735464.7, dated Apr. 14, 2010.
International Preliminary Report on Patentability for Application No. PCT/US2009/036343, dated Sep. 14, 2010.
International Search Report and Written Opinion for Application No. PCT/US09/36343, dated Jan. 7, 2010.
International Search Report and Written Opinion for Application No. PCT/US06/40621, dated May 18, 2007.
International Search Report for Application No. PCT/US06/05811, dated Sep. 13, 2007.
International Search Report for Application No. PCT/US2008/068515, 3 pages, dated Jan. 2, 2009.

* cited by examiner

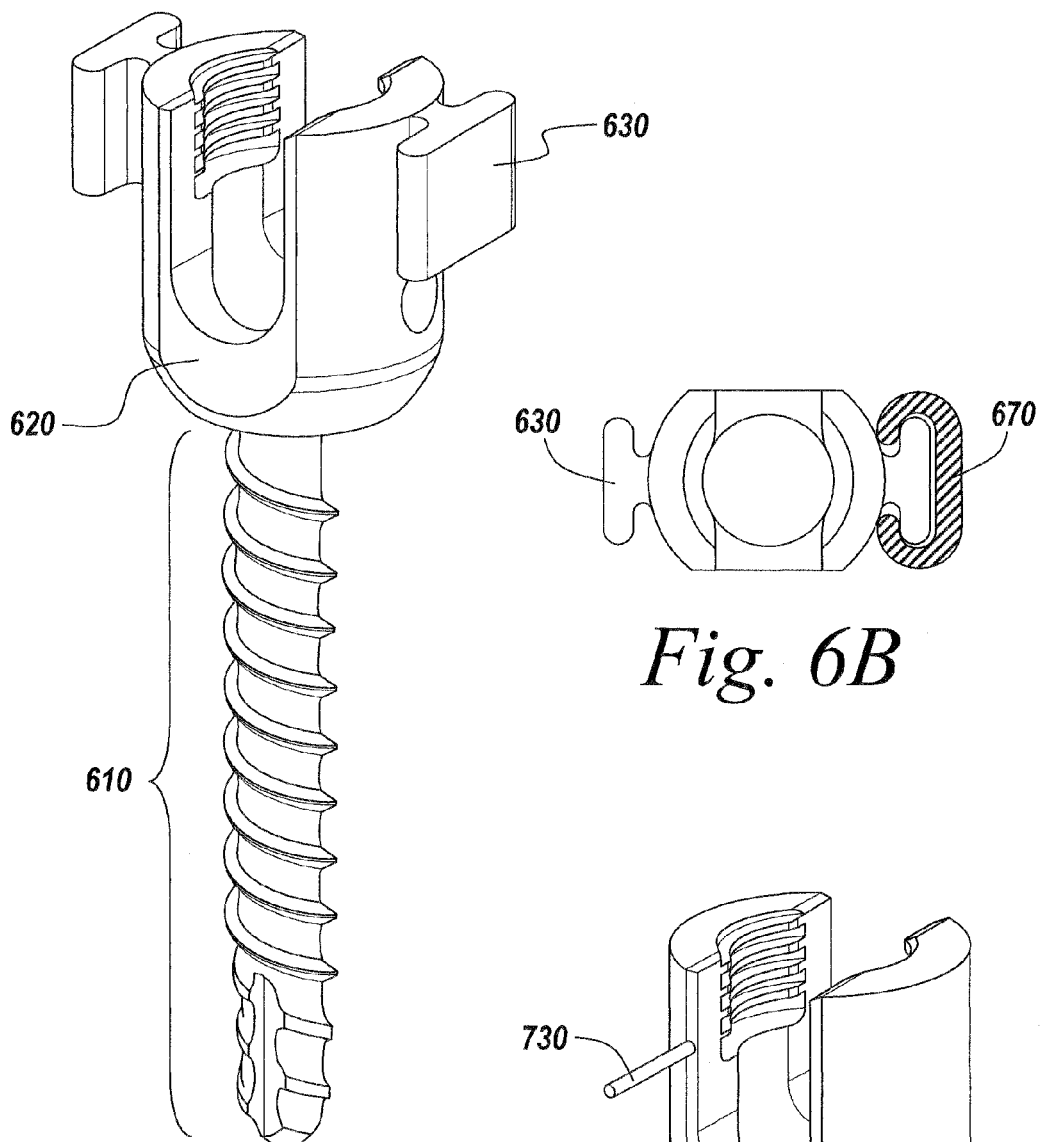

BILATERAL VERTEBRAL BODY DEROTATION SYSTEM

BACKGROUND

In spinal deformity surgical procedures, the curvature of the spine (e.g., the coronal curvature of the spine and/or the sagittal curvature of the spine) can be corrected by the implantation of a construct of bone anchors and spinal fixation elements. Examples of bone anchors used in such a construct include hooks and bone screws. Examples of spinal fixation elements used in such a construct include rods and tethers.

During spinal deformity surgical procedures, a surgeon typically first exposes the spine posterior and attaches bone anchors to selected vertebrae of the spine. The surgeon then inserts a spinal fixation element into receiving portions of the bone anchors to connect the selected vertebrae, thereby fixing the relative positions of the vertebrae.

In addition to correcting the curvature of the spine, the angular rotation of one or more vertebrae relative to other vertebrae around the axial plane of the vertebra may also be corrected. Conventional surgical procedures for correcting the angular relationship of a vertebra involve rotating the spinal fixation element, for example, a spinal rod, connected to the vertebra by a bone anchor. In the case of constructs that include a spinal rod, this procedure is typically referred to as "derotation." Derotation can place significant stress on the interface between the bone anchors connected to the rotated spinal rod and the vertebra in which each bone anchor is implanted. This stress can cause a failure of one or more of the bone anchors or harm to the vertebra. Accordingly, there is a need for improved instruments and methods for manipulating a vertebra.

Conventional derotation instruments are designed to be used after reduction has been performed and the spinal fixation element has been secured to the bone anchor. However, the bone anchors often bind on the fixation element during the rotation, preventing the motion or requiring significant force to obtain it. Thus in some instances it may be beneficial to perform derotation before insertion of the spinal fixation element. Being able to insert the rod after derotation reduces the need for significant reduction, complicated rod contouring and in-situ bending thereby decreasing the complexity of the procedure.

SUMMARY

Disclosed herein is a system for manipulating vertebral bodies. The system and methods disclosed herein are particularly suited to facilitate rotation of vertebrae to correct the rotational relationship between vertebrae while leaving the implants accessible for attaching a spinal fixation element. The instrument does not require the spinal fixation element to be inserted into the bone anchor prior to manipulation.

In accordance with one example embodiment, an instrument for manipulating vertebral bodies is provided. The instrument includes a first arm and a second arm connected to the first arm. The first arm has a proximal end and a distal end configured to engage a removable attachment element of a first implant assembly implanted in a pedicle of a vertebral body. The second arm has a proximal end and a distal end configured to engage a removable attachment element of a second implant assembly implanted bilaterally from the first bone anchor assembly implanted in the other pedicle of the vertebral body.

In accordance with another example embodiment, an implant assembly is provided for use in bilateral vertebral body manipulation. The implant assembly includes a bone anchor, a body, and a removable attachment element. The bone anchor has a proximal head and a distal shaft extending along a longitudinal axis configured to engage bone. The body is configured to engage the proximal head of bone anchor and receive a spinal fixation element. The removable attachment element is provided on the body for connecting the implant assembly to an arm of the instrument used to manipulate the implant assembly in a bilateral arrangement. Once manipulation is completed, the removable attachment element is detached from the body.

In accordance with another example embodiment, a system is provided for manipulating one or more vertebrae. The system includes at least two implant assemblies as described herein and an instrument as described herein configured to attach to the two bone screw assemblies for manipulating a vertebra into which the implant assemblies are implanted.

In accordance with another example embodiment, a method is provided for manipulating a vertebral body. The method includes the following steps: A first implant assembly having a removable attachment element is inserted into a vertebra. Then, a second implant assembly having a removable attachment element is inserted into the vertebra bilaterally from the first implant assembly. An instrument as described herein is then attached to the first and second implant assembly. Finally, the instrument may be used to manipulate the vertebra using the instrument attached to the first and second implant assemblies implanted bilaterally in the vertebra.

BRIEF DESCRIPTION OF THE FIGURES

FIG. 6A is a perspective view illustrating another embodiment of an attachment element of an implant assembly;

FIG. 6B is a top view of the instrument of FIG. 6A, illustrating the distal end of an instrument configured to engage the attachment element;

FIG. 7 is a perspective view illustrating another embodiment of an attachment element of an implant assembly;

DETAILED DESCRIPTION OF THE INVENTION

The disclosed embodiments provide a system including an implant assembly and an instrument configured to work in conjunction to manipulate vertebral bodies to affect derotation. The implant assemblies include an attachment element that allows for the attachment of the instrument. The instrument is configured to attach to two implant assemblies that have been inserted bilaterally into a vertebral body. When the instrument is attached to the implant assemblies, forces applied to the instrument are translated and transferred to the implant assemblies and the vertebral body into which the implant assemblies have been inserted thereby providing a rotational force on the vertebral body.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

Implant Assembly

Figure 1:
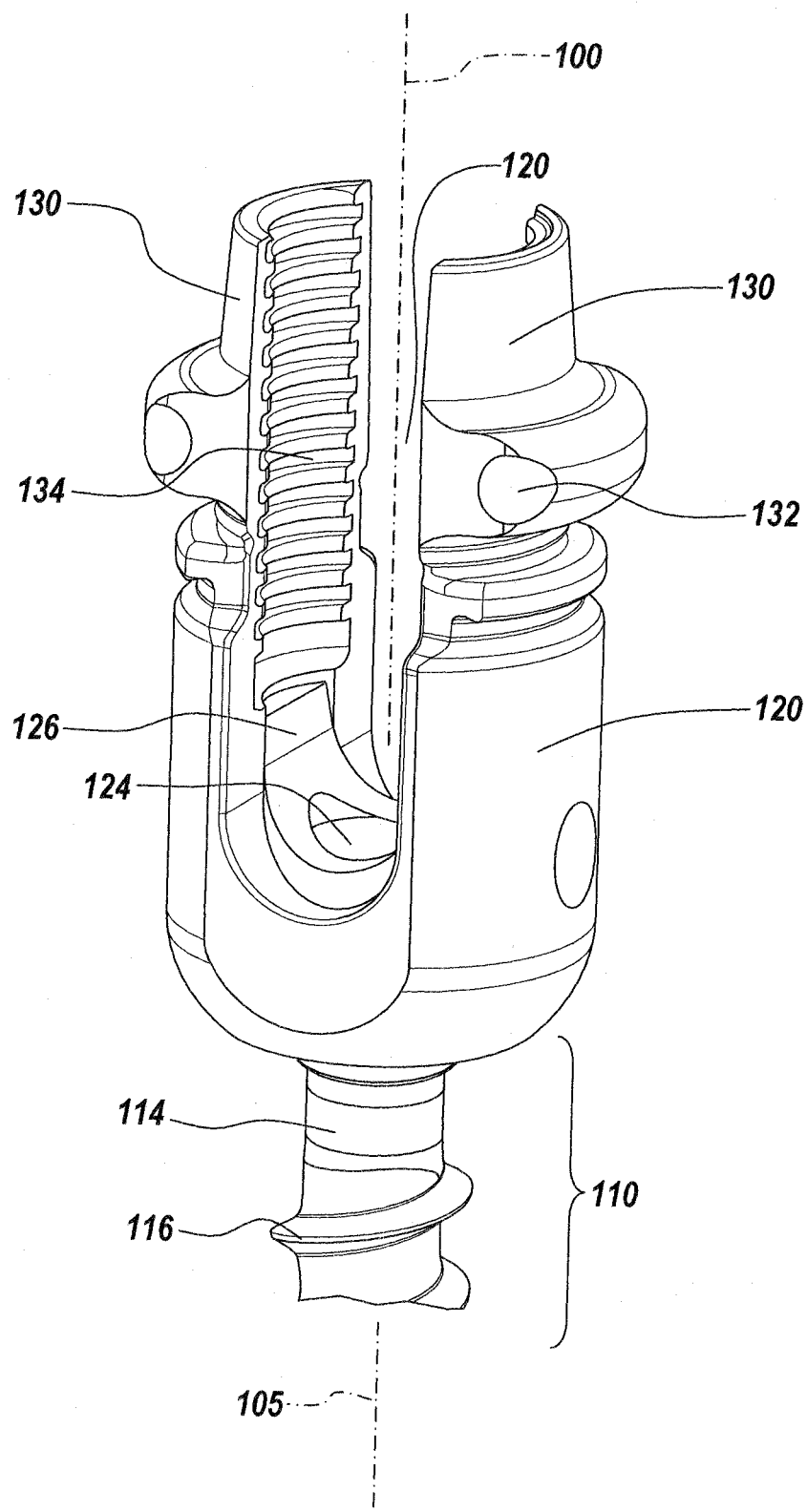
FIG. 1 is a perspective view illustrating an example embodiment of an implant assembly.

FIG. 1 depicts one embodiment of an implant assembly 100. FIG. 1A depicts an assembled view implant assembly 100. The implant assembly 100 includes a bone anchor 110, a body 120, and an removable attachment element 130. The bone anchor 110 has a proximal head not shown and a distal shaft 114 extending along a longitudinal axis configured to engage bone. The body 120 is configured to engage the proximal head of bone anchor 110 and receive a spinal fixation element (not shown). The removable attachment element 130 extends from the body 120 and is configured for connecting the implant assembly 100 to an instrument used to manipulate the implant assembly 100. Each of these elements will be described in more detail below.

The distal shaft 114 extends from the body 120 along a longitudinal axis 105. The distal shaft 114 is configured to engage bone. To assist in the engagement of bone, the distal shaft 114 may be provided with threads 116 or other engagement configuration.

In the example of FIG. 1, the implant assembly 100 is configured as an open head screw type. As such, the body 120 includes a U-shaped slot 122 for receiving a spinal fixation element, such as a rod (not shown). The body 120 further includes a passage 124 for receiving the bone anchor 110 and engaging the proximal head of the bone anchor 110. When assembled, the distal shaft 114 of the bone anchor 110 is passed through the passage 124 until the proximal head is engaged. The implant assembly 100 in this embodiment is a uniplanar or monoplanar screw; thus the body further includes a rod seat 226 that restrict the movement of the body 220 around the proximal head to one axis. In other embodiments, a monoaxial screw in which the body does not rotate at all in relation to the bone anchor may be used.

The removable attachment element 130 in this embodiment is a detachable tab extending from the body 120. In this embodiment, there is a detachable tab 130 on each side of the body 120. The tabs 130 effectively extend the U-shaped slot 122 of the body 120. The tab 130 further defines a thru-hole 132. The thru-hole provides a convenient attachment point for connecting an instrument to the implant assembly 100. The thru-hole 132 creates a pin joint. Pinjoints do not transfer moments (or rotational forces) and as such a derotation force applied to the tab 230 result in push or pull forces rather than bending of the tab 130 when derotation is performed using the described instruments and techniques disclosed herein The removable tabs 130 may be selectively detachable. This allows the tabs 130 to be removed after they have been used for de-rotation. By making the attachment elements 130 tabs extending from the body 120, the overall profile of the implant assembly 100 is maintained. Once the tabs 130 are detached, the implant assembly 100 resembles a traditional implant assembly 100 allowing the use of existing instruments with the implant assembly 100. In some embodiments, the tabs 130 may also include internal threads 134 allowing the tabs 130 to provide a certain degree or reduction of a spinal fixation element received in the U-shaped slot 122 of the body 120.

Figure 2:
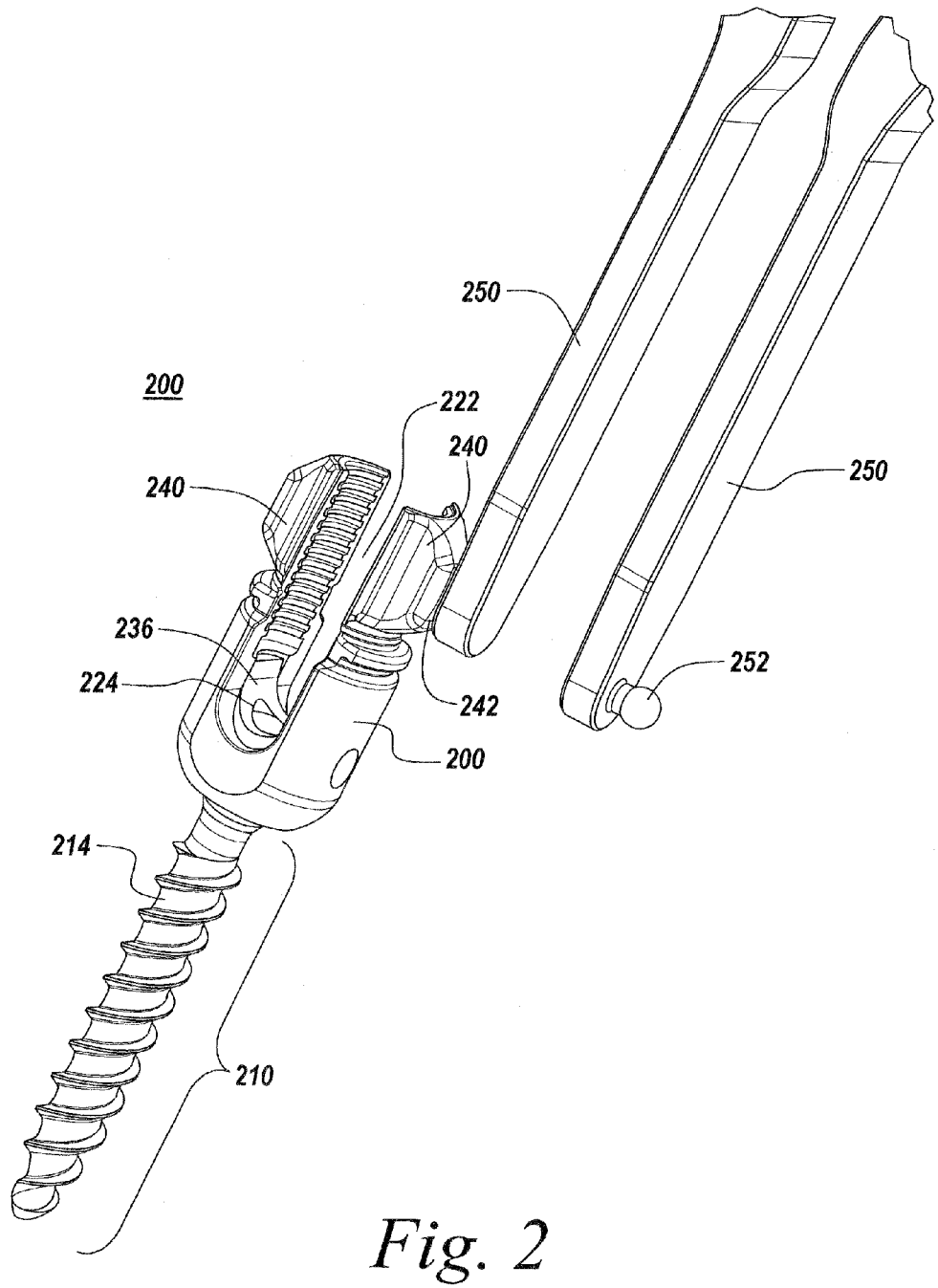
FIG. 2 is a perspective view illustrating another example embodiment of an implant assembly.

FIG. 2 depicts another embodiment with an alternate tab 240 configuration. The screw assembly 200 is largely the same as in FIG. 1. The implant assembly 200 includes a bone anchor 210 having a distal shaft 214 and a proximal head (not shown) connecting the bone anchor 210 to the body 220. The body 220 includes a U-shaped slot 222 for receiving a spinal fixation element, such as a rod (not shown). The body 220 further includes a passage 224 for receiving the bone anchor 210 and engaging the proximal head of the bone anchor 210. The implant assembly 200 in this embodiment is also a uniplanar or monoplanar screw. Thus, the body further includes a rod seat 226 that restrict the movement of the body 220 around the proximal head to one axis.

In the embodiment of FIG. 2, the removable attachment elements 240 are tabs extending from the body 220 of the implant assembly 200. However, in this embodiment the tabs 240 include a spherical undercut feature instead of a thru-hole. The arms 250 of the instrument in turn are provided with a spherical connection element 252 that engage the spherical undercut feature. The spherical shape of the undercut feature and the connection element provide many of the same benefits as the pin joint in the embodiment of FIG. 2A.

Figure 3:
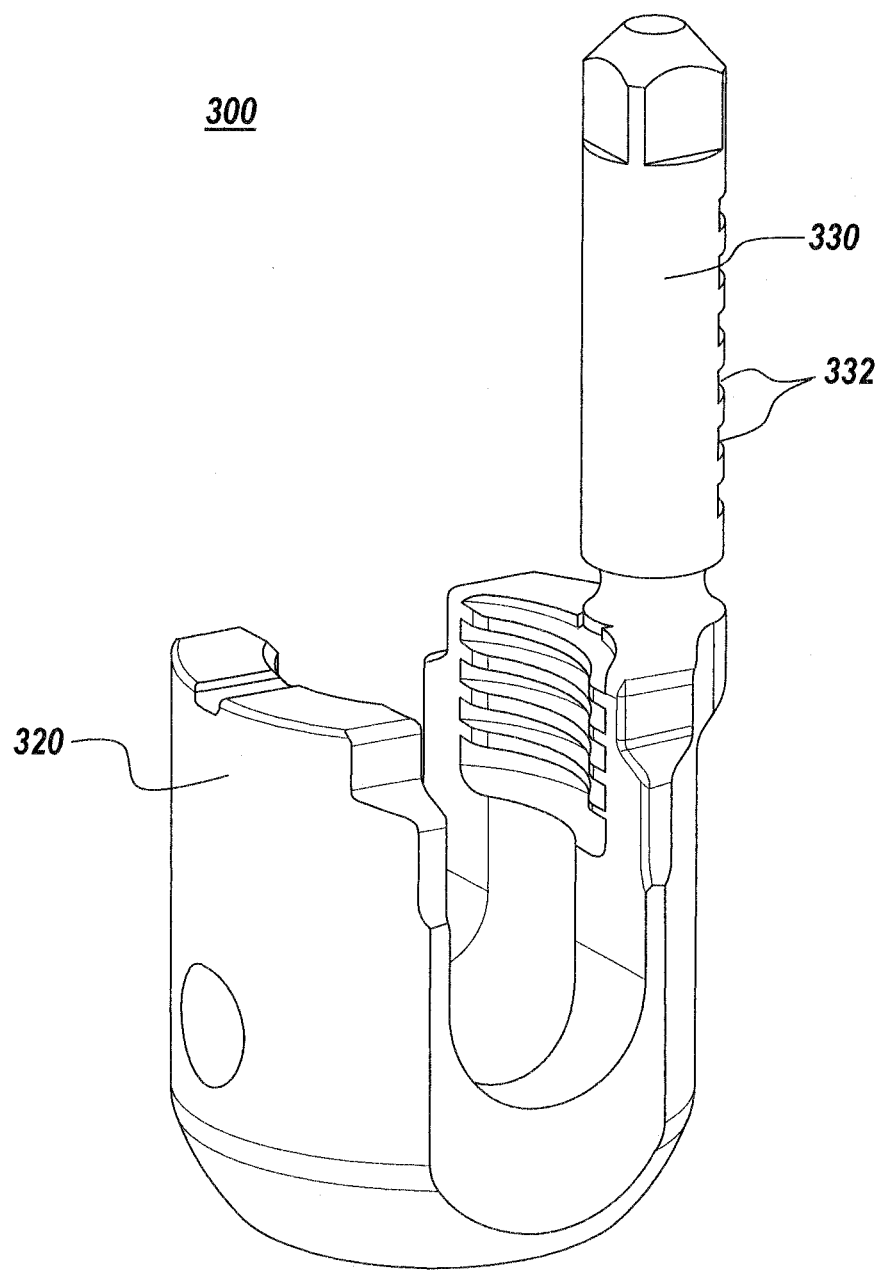
FIG. 3 is a perspective view illustrating another example embodiment of an implant assembly.

FIG. 3 depicts another alternate configuration for a connection element 330. In this embodiment, the connection element is a post 330 extending from the body 320 of the implant assembly 300 having a cylindrical shape. In this embodiment, the instrument (not shown) passes over the post to engage the implant assembly 300. The post 330 may be provided with surface features 332 such as threads, or grooves to keep the instrument engaged with the implant assembly during derotation. The post 330 is selectively detachable from connector body 320. Once the post 330 is detached, the implant assembly 300 resembles a traditional implant assembly 300 allowing the use of existing instruments with the implant assembly 300.

FIGS. 4-7 depict various embodiments wherein the attachment element may take on a number of geometries and configurations.

Figure 4:
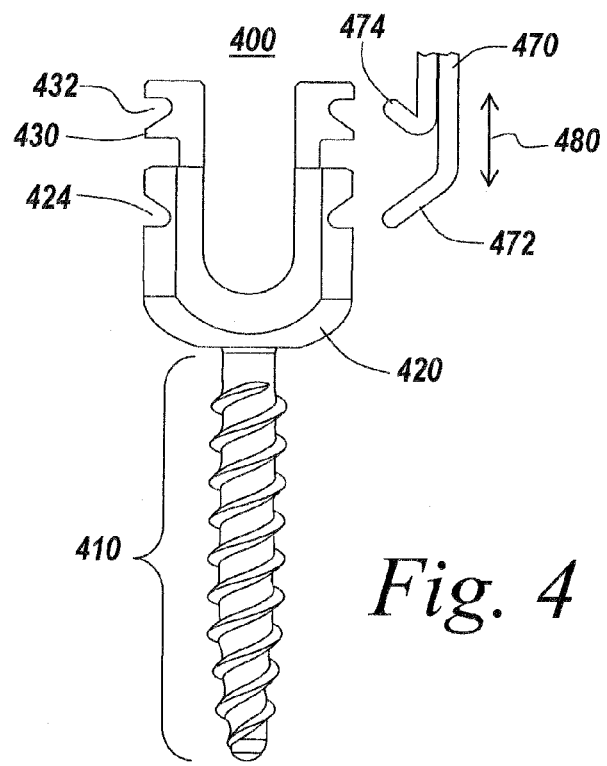
FIG. 4 is a side view illustrating another embodiment of an attachment element of an implant assembly and an end of instrument configured to engage the attachment element.

In the example of FIG. 4, the implant assembly 400 includes bone anchor 410, a body 420, and removable attachment elements 430. The bone anchor 410 and body 420 are similar to those previously discussed. The body 420 further includes engagement feature 424 that works in conjunction with the removable attachment elements. The attachment elements 430 in this example include tabs extending from the body including attachment features 432. Here the engagement features 424, 432 are notches that angled away from each other. The notches 424 on the body 420 are angled away from the notches 432 of the tabs 430 with are in turn angled away from the notches 424 of the body 420. The end(s) of an instrument 470 may be configured to engage the notches 424 and 432. In the example, the end(s) of the instrument 470 includes a first portion 472 and second portion 474 configured to engage the notches 424 and 432. Here, the attachment of the end of the instrument 470 is achieved through distraction. Thus, the first portion 472 and second portion 474 are slid relative to each other in the direction indicated by arrow 480 to secure the attachment. After derotation has occurred using the instrument, the tabs 430 may be detached from the body 420.

Figure 5:
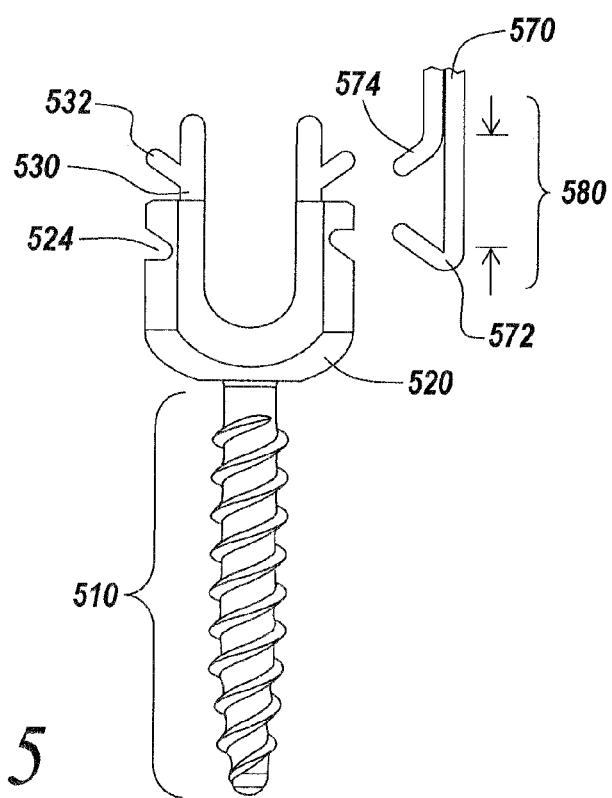
FIG. 5 is a side view illustrating another embodiment of an attachment element of an implant assembly and an end of instrument configured to engage the attachment element.

In the example of FIG. 5, the implant assembly 500 includes bone anchor 510, a body 520, and removable attachment elements 530. The bone anchor 510 and body 520 are similar to those previously discussed. The body further includes engagement feature 524. The removable attachment elements 530 in this example are tabs extending from the body 520 having further engagement features 532. Here the engagement features 524, 532 are notches that angled toward each other. The notches 524 on the body 520 are angled toward the notches 532 of the tabs 530 with are in turn angled toward the notches 524 of the body 520. The end(s) of an instrument 570 may be configured to engage the surface configurations 532 on the tabs 530 in combination with an annular ring 524 on the body 520. In the example, the end(s) of the instrument 570 includes a first portion 572 and second portion 574 configured to engage the surface configurations 532 and the annular ring 524. Here, the attachment of the end of the instrument 570 is achieved through compression. Thus, the first portion 572 and second portion 574 are slid relative to each other in the direction indicated by arrows 580 to secure the attachment. After derotation has occurred using the instrument, the tabs 530 may be detached from the body 520.

FIG. 6A and 6B depict another embodiment of an implant assembly 600. FIG. 6A is a perspective view of the implant assembly 600. FIG. 6B is a top view of the implant assembly 600 showing the end of an instrument 670 configured to attach to the implant assembly 600. The implant assembly 600 includes bone anchor 610, a body 620, and removable attachment elements 630. The bone anchor 610 and body 720 are similar to those previously discussed. The removable attachment elements 630 in this example are tab extending from the body 620. The end(s) of an instrument 670 may be configured to engage the tabs 630. In some embodiments, the instrument 670 could be provided with a clearance fit between the tabs 630 and the body 620. Alternately, the spacing between the tabs 630 and the body 620 could taper providing a wedging effect when the instrument 670 is attached. In other embodiments, the instrument 670 could be tapered to create the wedging effect. Once derotation has occurred, the tabs 630 may be selectively detached from the body 620.

In the example of FIG. 7, the implant assembly 700 includes bone anchor 710, a body 720, and removable attachment elements 730. The bone anchor 710 and body 720 are similar to those previously discussed. The attachment elements 830 in this example comprise one or more pins extending from the body 720. The pins may operate similar to thru holes but instead of the instrument having pins to engage the thru holes on the body, the instrument has thru holes for engaging pins on the body. Once derotation has occurred, the pins 730 may be removed from the body 720.

While, the previous examples have focused on poly-planar or mono-planar screws having open heads, it should be understood that the implant assembly have a closed head or a mono-axial screw. Other embodiments, configurations, and applications will be apparent to one skilled in the art given the benefit of this disclosure.

The components of the implant assembly of the illustrative embodiments of the invention may be manufactured from any suitable biocompatible material, including, but not limited to, metals and metal alloys such as titanium and stainless steel, polymers and/or ceramics. The components may be manufactured from the same or different materials though manufacturing processes known in the art.

Instrument

Figure 8:
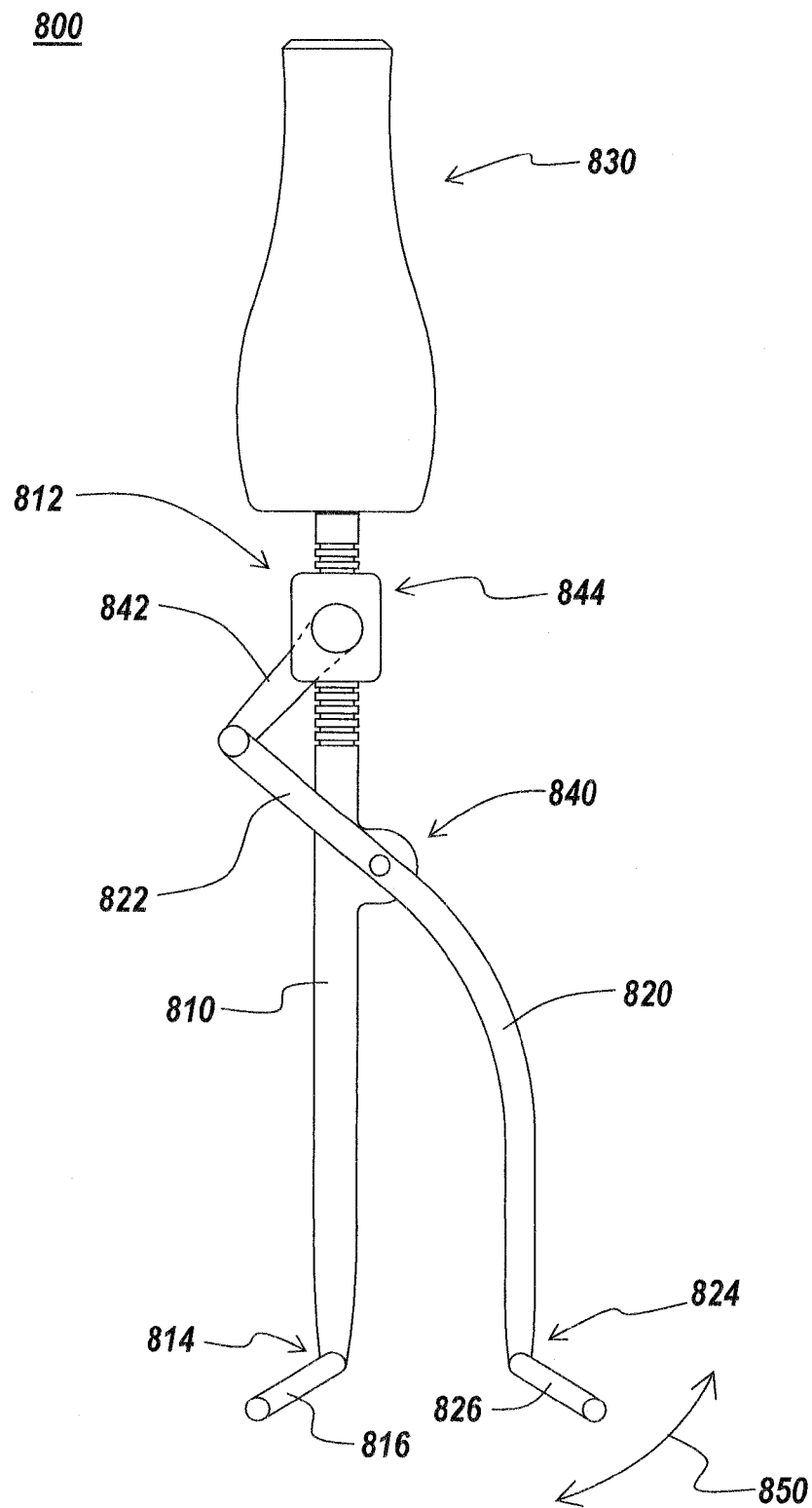
FIG. 8 is a perspective view illustrating one embodiment of an instrument used to manipulate a vertebral body.

FIG. 8 depicts one embodiment of an instrument 800 used for manipulating vertebra. The instrument 800 includes a first arm 810 and a second arm 8920 pivotly connected to the first arm 810. The first arm has a proximal end 812 and a distal end 814. The distal end 814 is configured to engage a first implant assembly as discussed above. The second arm 820 also has a proximal end 822 and a distal end 824. The distal end 822 of the second arm 820 is configured to engage a second bone screw as discussed above.

In certain embodiments, the instrument may further include a handle 830 disposed at the proximal end of at least one of the first or second arms. In the example of FIG. 8, the handle 830 is attached to the proximal end 812 of the first arm 810. The handle provides a user a convenient area to grip the instrument 800 and apply force for manipulating a vertebra.

In this example, the second arm 820 is attached to the first arm at a pivot 840. The proximal end 822 of the second arm 820 is further pivotably connected to a support arm 842, which is pivotably connected to a push button or ratchet mechanism 844 on the first arm 810. When the push button or ratchet mechanism 844 is moved along the length of the first arm 810, the connected support arm 842 transfers the motion to the proximal end 822 of the second arm. This causes the second arm 820 to rotate around pivot 840. This results in the distal end 824 of the second arm 820 moving toward or away from the distal end 814 of the first arm 810 in the direction indicated by arrow 850.

As the distal ends 814, 824 of the first and second arms 810, 820 are configured to engage implant assemblies as previously discussed, the distal ends 914, 924 may be provided with specifically configured feet 816, 826 for engaging the attachment element of the implant assembly. In the example of FIG. 8, the feet 816, 826 are pins for engaging thru holes provided on an implant assembly. Other examples of feet and distal ends of instrument have been shown in FIGS. 2 and 4-6. Still other embodiments and configurations will be apparent to one skilled in the art given the benefit of this disclosure.

Figure 9:
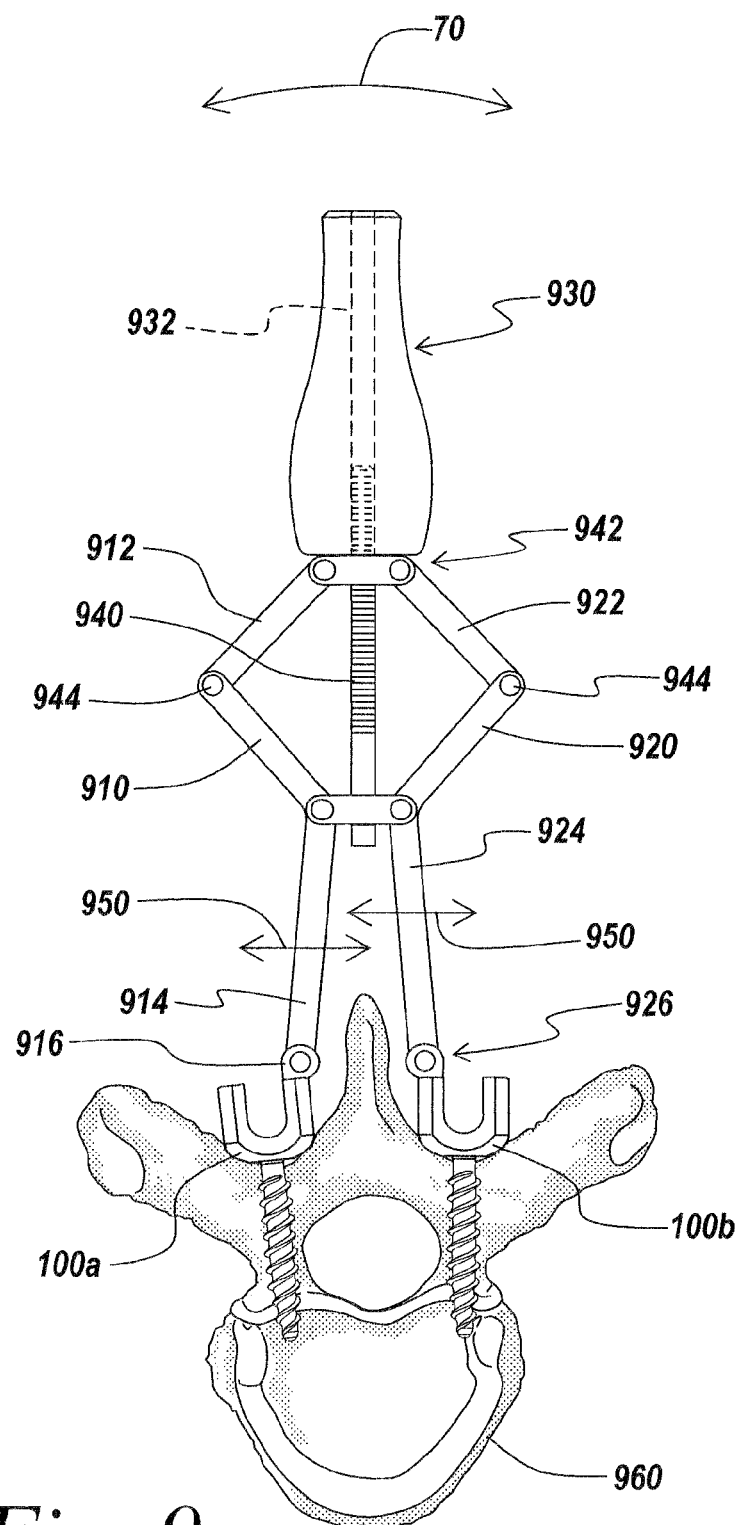
FIG. 9 is a perspective view illustrating another embodiment of an instrument used to manipulate a vertebral body.

FIG. 9 depicts another embodiment of an instrument 900. In this example, the distal ends 912 and 922 of the first arm 910 and second arm 920 are connected to a central shaft 940 as well as an adjustment mechanism 942 that rides along the central shaft 940. Both the first arm 910 and second arm 920 also include pivots 944. The handle 930 is connected to the adjustment mechanism 942. The handle includes a central bore 932 that allows the handle 930 to receive the central shaft 940. In this embodiment, the handle 930 also is used to control the spacing of the first and second arm 910, 920. By advancing or retracting the handle 930 along the central shaft 940, the adjustment mechanism 942 is moved along the central shaft 940. This movement is translated through pivots 944 and the pivotable connection to the central shaft 940 into movement of the distal ends 914, 916 in the direction indicated by arrows 950.

In the example of FIG. 9, the instrument has been attached to a first implant assembly 100a and a second implant assembly 100b inserted bilaterally in a vertebra 960. This allows the vertebra to be manipulated by moving the handle 1130 in the direction indicated by arrow 1170 to effect derotation.

The first implant assembly 100a is attached to the first arm 910 and the second implant assembly 100b is attached to the second arm 920. Here the feet 916, 926 are configured to engage the respective attachment element of the respective implant assembly 100a, 100b. A close-up of the interconnection between a foot of the instrument and the attachment element of the implant assembly can be seen in FIG. 10.

Figure 10:
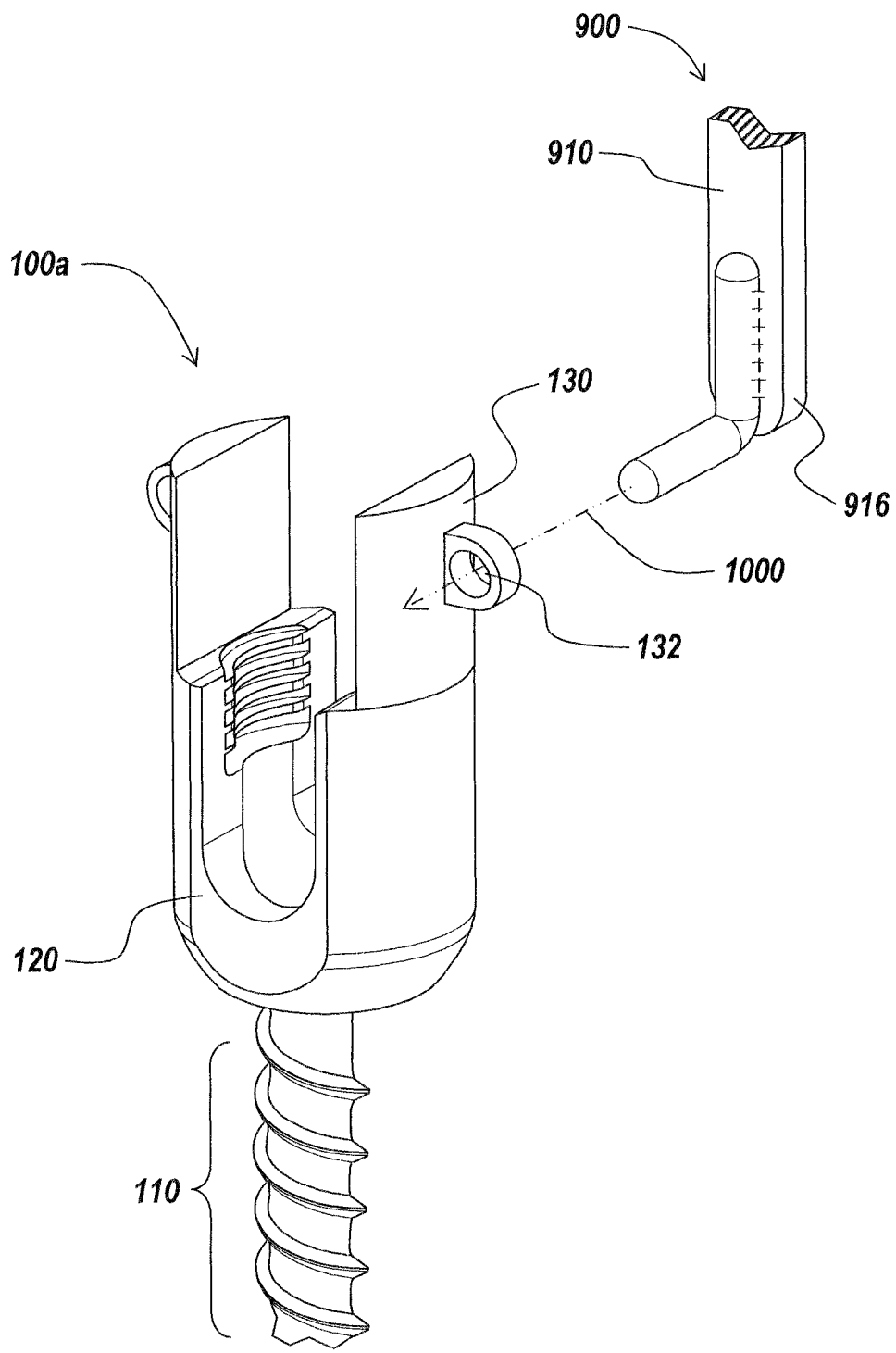
FIG. 10 is a close-up perspective view illustrating the attachment of the instrument of FIG. 9 to an implant assembly.

In FIG. 10, the foot 916 of the first arm 910 of the instrument 900 is configured as a pin to engage a thru hole 132 in the removable attachment element 130 extending from the body 120 of the first implant assembly 100a. Dashed line 1000 indicated a possible trajectory for the insertion of the pin into the thru-hole 132. As discussed previously, the thru-hole 132 provides a convenient attachment point for connecting an instrument to the implant assembly 100. The thru-hole 132 creates a pin joint. Pin joints do not transfer moments and as such, a rotational force applied to the instrument results in push or pull forces rather than bending of the tab 130. Depending on the implementation, the implant assemblies 100a and 100b may be at different relative heights, angles, and rotations. Pin joints accommodate these variations better than many other geometries.

The adjustment of the spacing and positions of the first and second arms can be handled in a number of ways. FIGS. 11-14 depict a number of embodiments of instruments with different positioning mechanisms.

Figure 11:
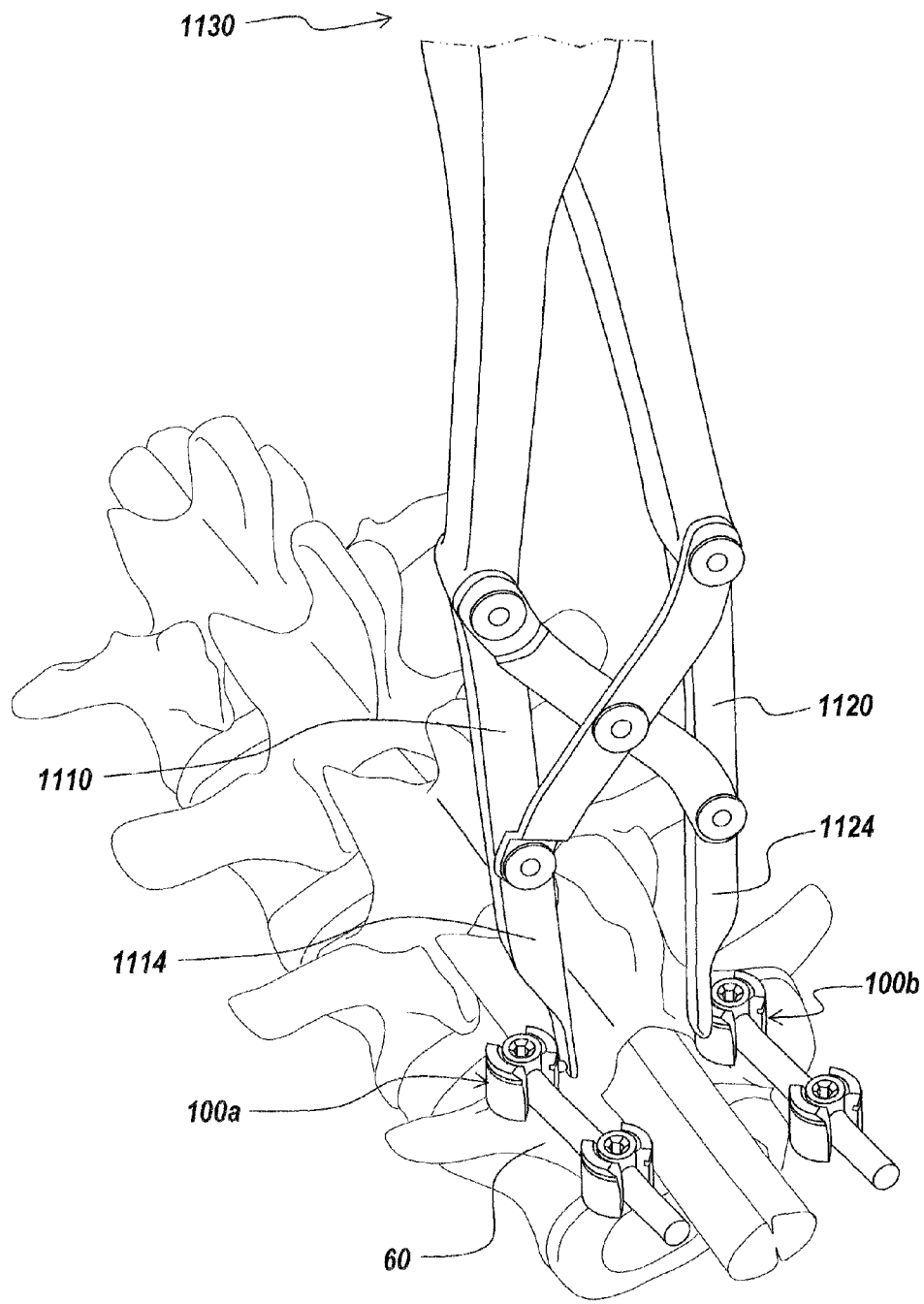
FIG. 11 is a perspective view illustrating another embodiment of an instrument used to manipulate a vertebral body.

In FIG. 11, the instrument is a modified parallel distractor used with the Expedium® screw system made by Depuy Spine. The spacing of the arms 1110, 1120 is actuated by squeezing the proximal handle 1130. The distal ends 1114, 1124 have been modified to engage attachment elements 130 on the bilaterally implanted first and second implant assemblies 100a, 100b.

Figure 12:
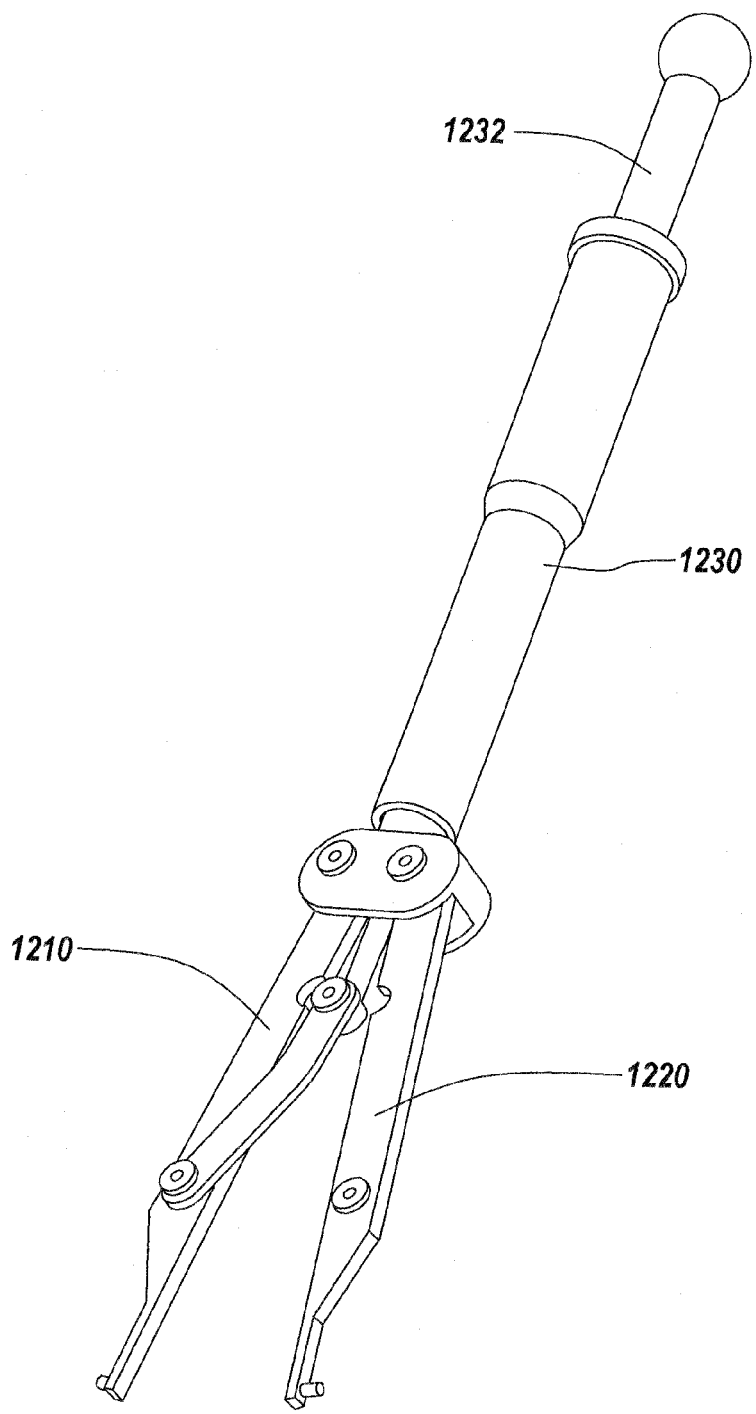
FIG. 12 is a perspective view illustrating another embodiment of an instrument used to manipulate a vertebral body.

In FIG. 12, the spacing of the first arm 1210 and second arm 1220 is controlled be a mechanism 1232 in the handle 1230. In this example, the mechanism 1232 is a plunger mechanism. By actuating the plunger 1232 in the handle 1230, the spacing of the first and second arms 1210, 1220 is actuated.

Figure 13:
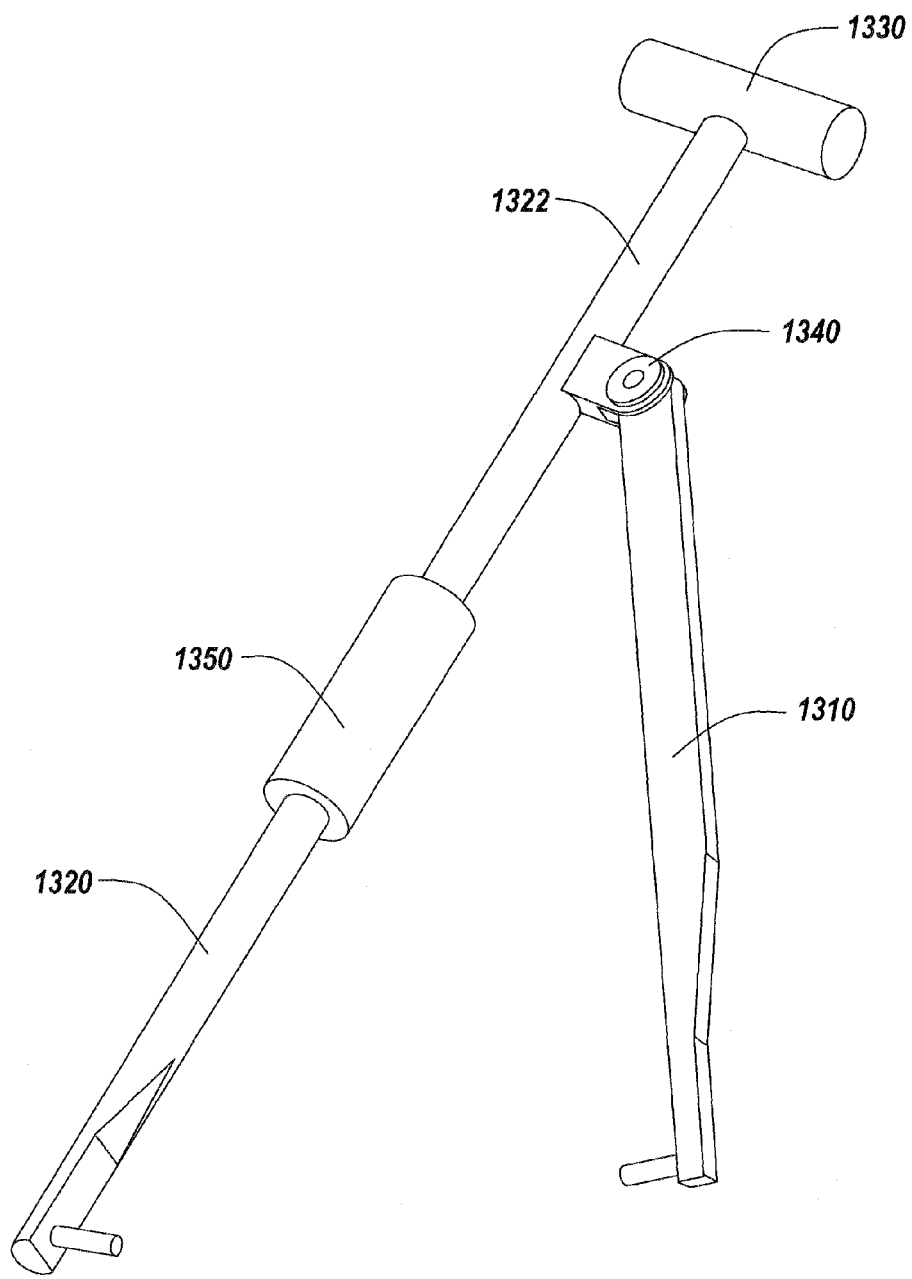
FIG. 13 is a perspective view illustrating another embodiment of an instrument used to manipulate a vertebral body.

In FIG. 13, the second arm 1320 is connected to the first arm 1310 at apivot 1340. The handle 1330 is attached to the proximal end of the second arm 1320. A turnbuckle 1350 is provided on the second arm 1320 to affect derotation. The first arm 1310 is connected to a first implant in a first pedicle of a vertebra and the second arm 1320 is connected to a second implant in the second pedicle of the vertebra. When, the turnbuckle 1350 is rotated, the length of the second arm is adjusted. Since the first arm 1310 and second arm 1320 are pivotly attached to each other, the adjustment of the length of the second arm 1320 causes the vertebra to rotate, thus derotating the vertebra.

Figure 14:
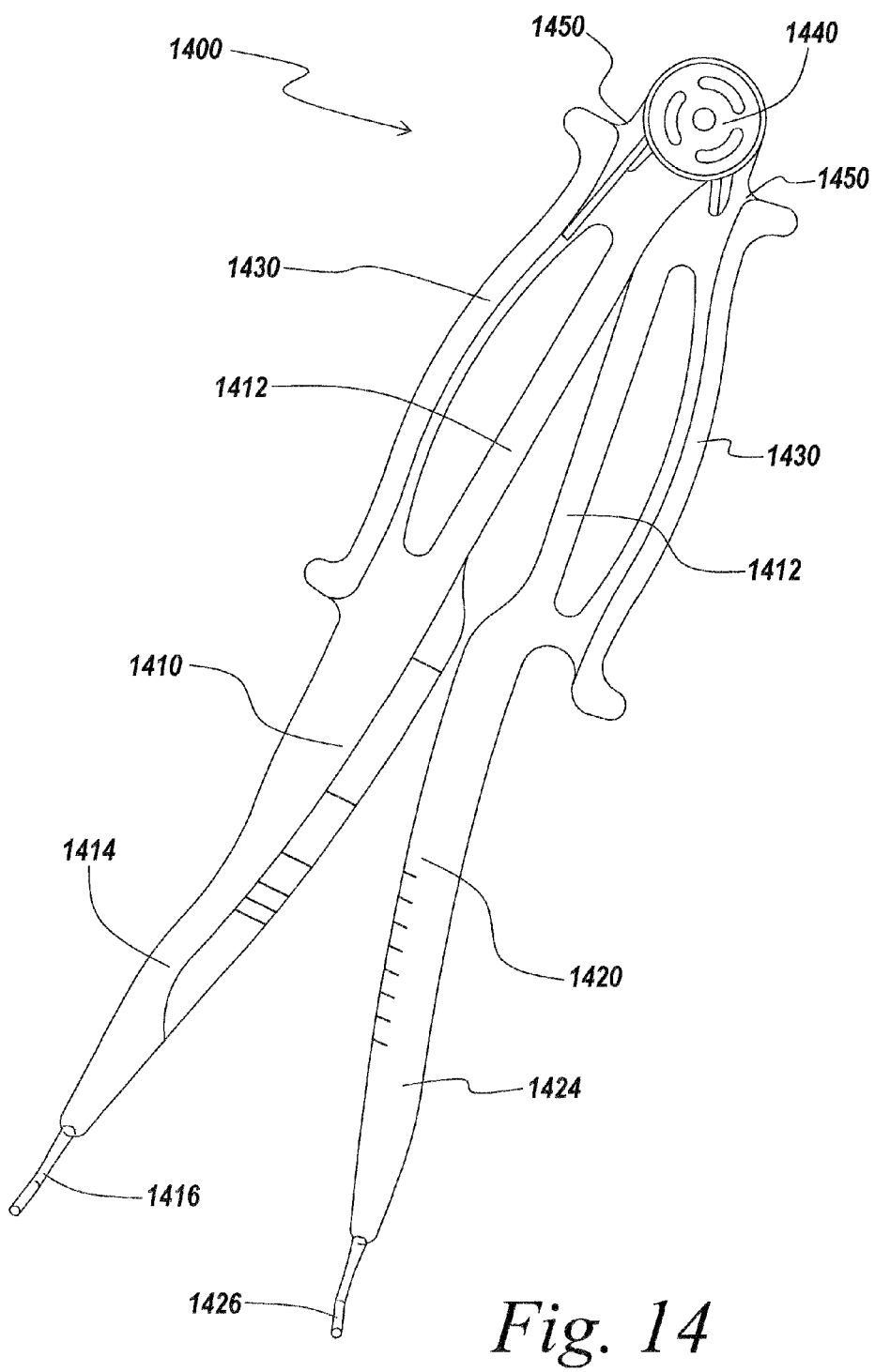
FIG. 14 is a perspective view illustrating another embodiment of an instrument used to manipulate a vertebral body.

In FIG. 14, the first arm 1410 and the second arm 1420 are connected at their respective proximal ends 1412, 1422 by a pivot 1440 providing a caliper type configuration. The proximal ends 1412, 1422 also form the handle 1430 in this configuration. The distal ends 1414, 1424 are provided with feet 1416, 1426 having pins configured to engage thru holes of an attachment element of the implant assembly described above. In this embodiment, the instrument 1400 further includes one or more connection elements 1450 for connecting instrument to a connector, such as an alignment rod (not shown).

The components of the instrument of the illustrative embodiments may be manufactured from any suitable material, including, but not limited to, metals and metal alloys such as titanium and stainless steel, polymers and/or ceramics. The components may be manufactured from the same or different materials though manufacturing processes known in the art.

Methods of Use

Figure 15:
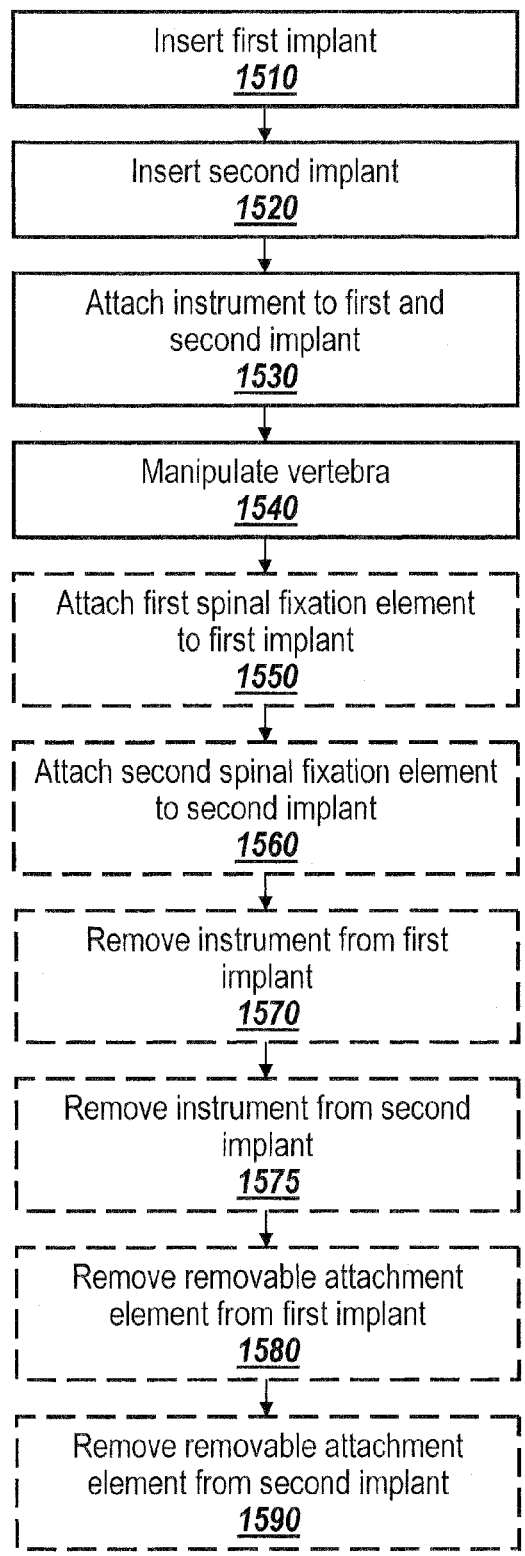
FIG. 15 is flow chart illustrating one embodiment of manipulating a vertebra using the implant assemblies and instruments disclosed herein.

FIG. 15 depicts an example flowchart 1500 of one embodiment of a method used for manipulating a vertebral body. The method includes inserting a first implant bilaterally into a vertebra (step 1510). A second implant assembly may then be inserted into the vertebra bilaterally from the first implant assembly (step 1520). An instrument may then be attached to the first and second implant assemblies (step 1530). Once the instrument has been attached, the vertebra may then be manipulated using the instrument (step 1540). In certain embodiments, the method may further include the steps of attaching a first spinal fixation element to the first implant assembly (step 1550) and attaching a second spinal fixation element to the second implant assembly (step 1560). After the first and second spinal fixation elements have been attached, the instrument may be removed from the first implant assembly (step 1570) and the second implant assembly (step 1575). After the instrument has been removed, the removable attachment element of the first and second implant assemblies may be removed (steps 1580 and 1590).

Figure 16A:
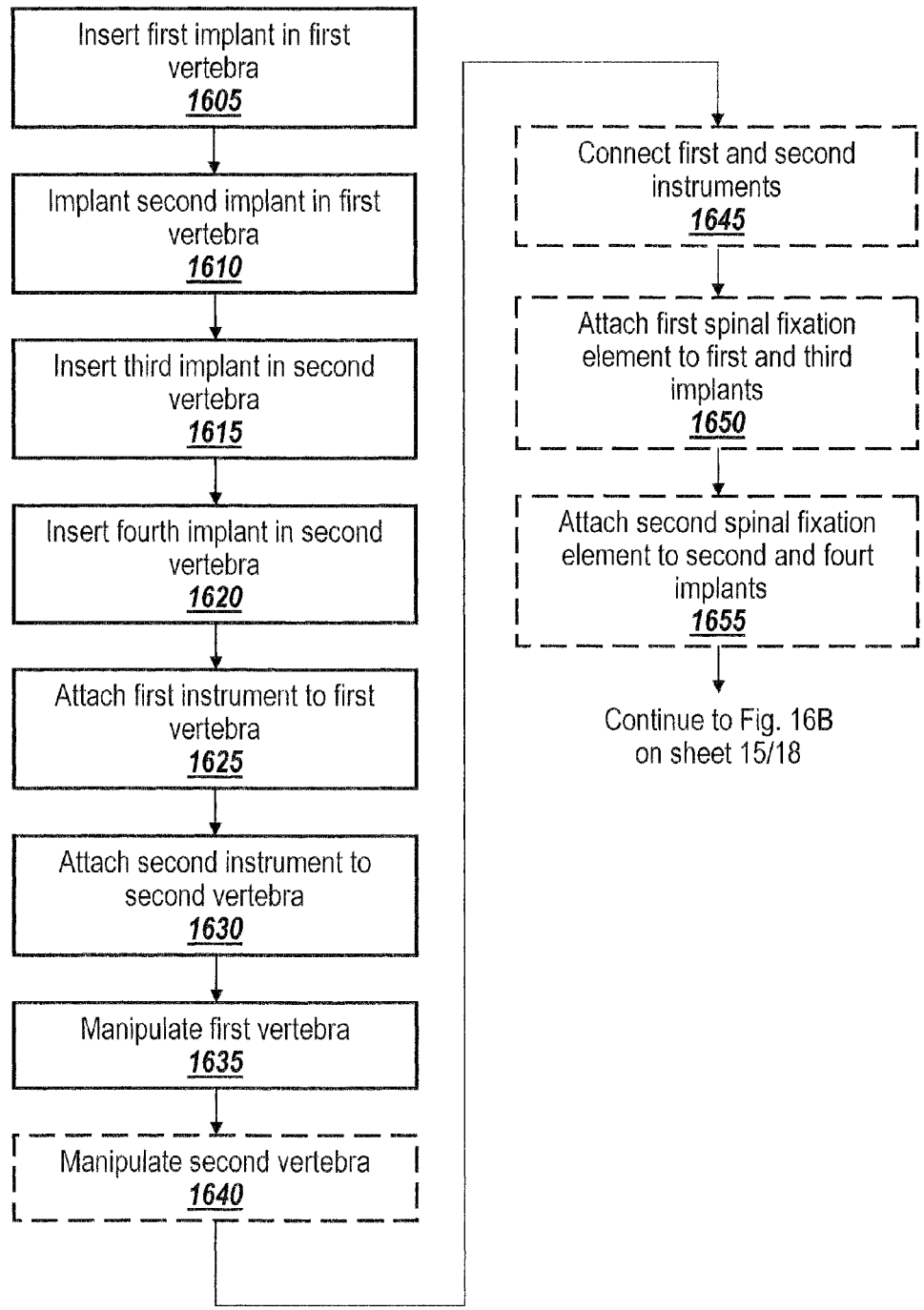
FIGS. 16A and 16B are a flow chart illustrating one embodiment of manipulating a vertebra using the implant assemblies and multiple instruments disclosed herein.
Figure 16B:
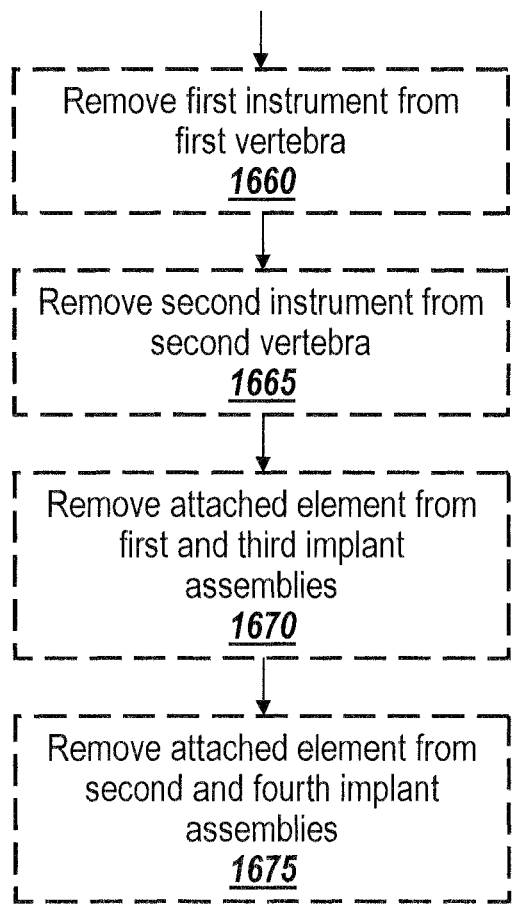

FIG. 16 depicts an example flowchart 1600 of one embodiment of a method used for manipulating multiple vertebral bodies. The method includes inserting a first implant bilaterally into a first vertebra (step 1605). A second implant assembly may then be inserted into the first vertebra bilaterally from the first implant assembly (step 1610). A third implant assembly may be inserted bilaterally into a second vertebra (step 1615). A fourth implant assembly may then be inserted bilaterally from the third implant assembly (step 1620). A first instrument may then be attached to the first and second implant assemblies (step 1625). A second instrument may also be attached to the third and fourth implant assemblies (step 1630). Once the first instrument has been attached, the first vertebra may then be manipulated using the first instrument (step 1635). Once the second instrument has been attached, the second vertebra may also be manipulated using the second instrument (step 1640). In certain embodiments, the method may also include connecting the first instrument to the second instrument using a connector (step 1645). In still other embodiments, the method may also include the steps of attaching a first spinal fixation element to the first and third implant assemblies (step 1650) and attaching a second spinal fixation element to the second and fourth implant assemblies (step 1655). After the first and second spinal fixation elements have been attached, the instrument may be removed from the first and second implant assembly of the first vertebra (step 1560) and the second instrument may be removed from the third and fourth implant assembly of the second vertebra (step 1565). After the first and second instrument has been removed, the attachment element of the first and third implant assemblies in may be removed (steps 1570) as well as the attachment elements of the second and fourth implant assemblies (1675).

Figure 17:
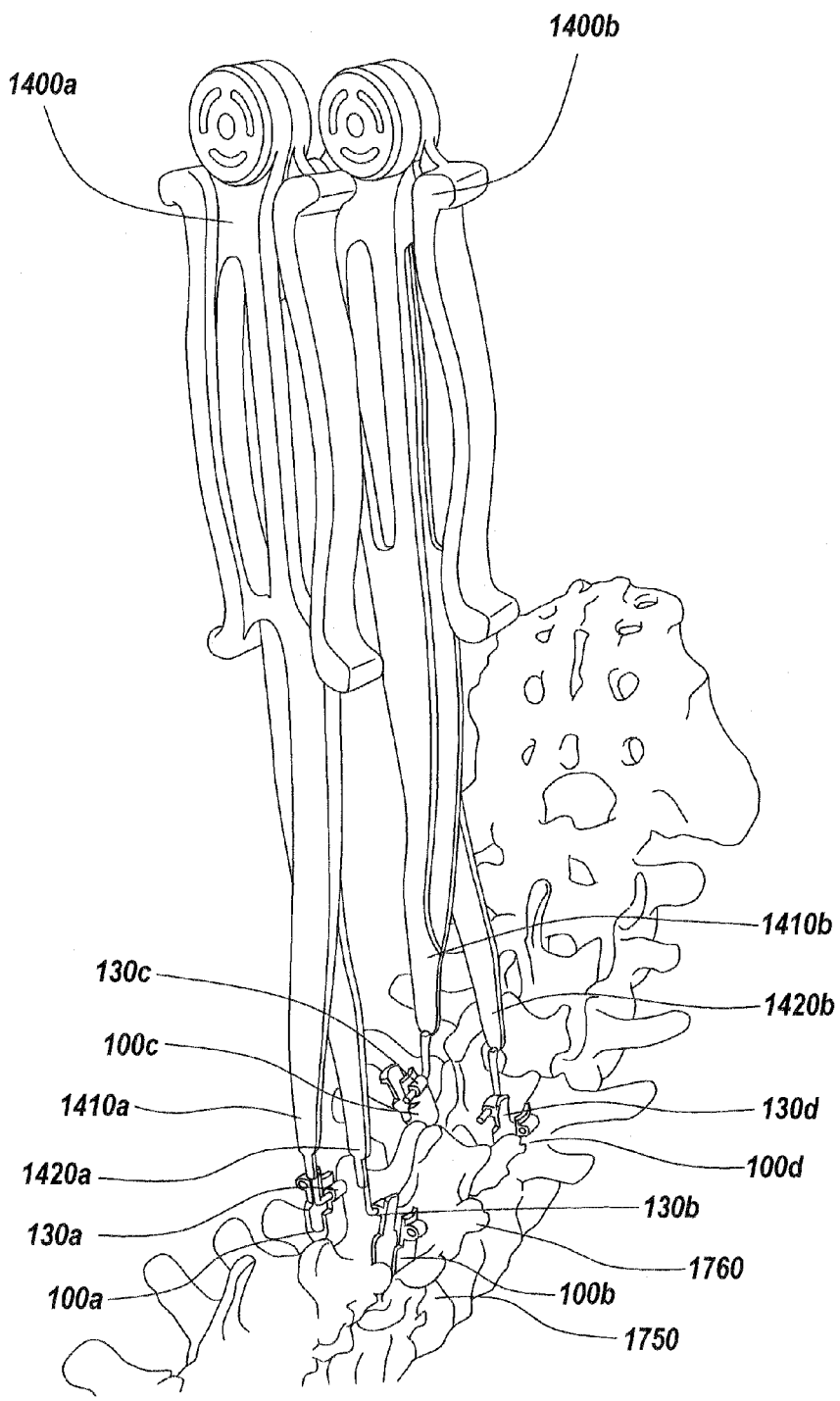
FIG. 17 if side view illustrating the manipulation of vertebra as set forth in the method of FIGS. 16A and 16B.

FIG. 17 depict the manipulation of a two vertebrae using two instruments and implant assemblies described previously. The instruments 1400a, 1400b are the caliper type as describe in relation to FIG. 14. The implant assemblies 100a, 100b, 100c, 100d are of the type described in relation to FIG.

1. However, it should be understood that any of the embodiments of the implant assemblies or instrument may be used.

In this example, the first and second implant assemblies 100a, 100b have been inserted bilaterally into the first vertebra 1750. The third and fourth implant assemblies 100c, 100d have been inserted bilaterally into the second vertebra 1760. The distal end 1414a of first arm 1410a of the first instrument 1400a is attached to the attachment element 130a of the first implant assembly 100a. The distal end of the second arm 1420a of the first instrument 1400a is attached to the attachment element 130b of the second implant assembly 100b. The distal end of first arm 1410b of the second instrument 1400b is attached to the attachment element 130c of the third implant assembly 100c. The distal end of the second arm 1420b of the second instrument 1400b is attached to the attachment element 130d of the fourth implant assembly 100d.

With the first and second instruments 1400a, 1400b attached, the first and second vertebra 1750, 1760 may be manipulated individually or together in relation to each other or to other vertebrae. In the example of FIG. 17, the first instrument 1400a has been used to orientate the first vertebra 1750 in relation to the second vertebra 1760 and both the first and second instruments 1400a, 1400b are used together to orientate the first and second vertebra 1750, 1760 in relation to the other vertebra.

As discussed previously, instruments may be provided with a connection element allowing the instrument to connect to a connector. Multiple instruments may thus be connected to the same connector (step 1645 of FIG. 16). An example of this can be seen in FIG. 18.

Figure 18:
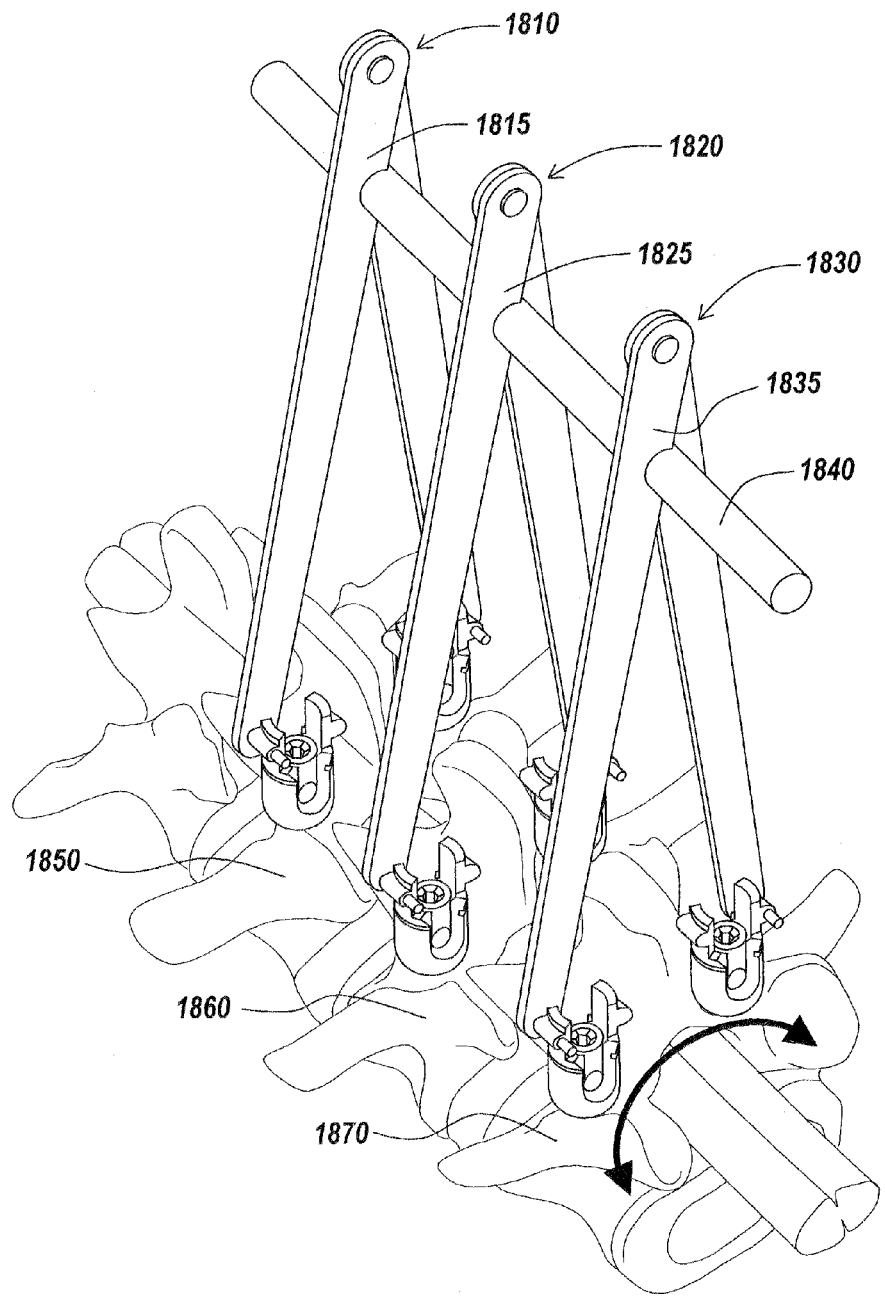
FIG. 18, is perspective view illustrating one embodiment of the connection of multiple instruments to a connector.

FIG. 18 depicts a perspective view of multiple instruments connected to the same connector 1840, such as an alignment rod. A first instrument 1810 is attached to a first vertebra 1850 for manipulating the first vertebra 1850. A second instrument 1820 is attached to a second vertebra 1860 for manipulating the second vertebra 1860. A third instrument 1830 is attached to a third vertebra 1870 for manipulating the third vertebra 1870. The first instrument 1810 is provided with a connector element 1815 for connecting the first instrument 1810 to the alignment rod 1840. The second instrument 2220 is provided with a connector element 2225 for connecting the second instrument 1820 to the alignment rod 1840. The third instrument 1830 is provided with a connector element 1835 for connecting the third instrument 1830 to the alignment rod 1840. By connecting each of the instruments 1810, 1820, 1830 to the alignment rod 1840, the orientation of each of the vertebra 1850, 1860, 1870 in relation to each other can be maintained while further manipulation or attachment of a spinal fixation element is performed. In some embodiments, multiple connectors 1840 may be used. In certain embodiments, the connector 1840 may be connected to operating table to provide a fixed location for the connecter 1840. An example of this can be seen in FIG. 19.

Figure 19:
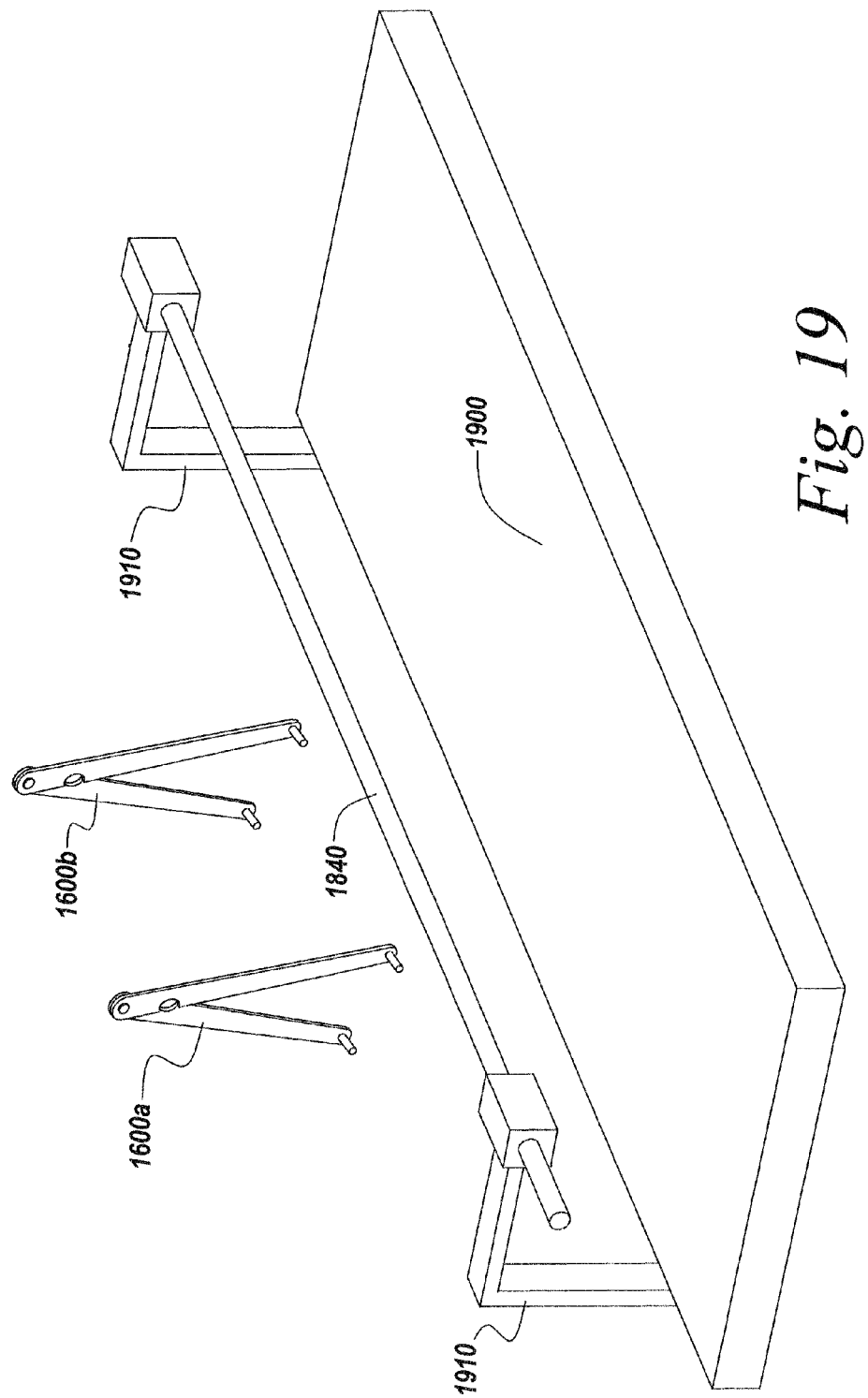
FIG. 19 is a perspective view of an assembly wherein the connector is attached to an operating table.

FIG. 19 depict and example of an operation table 1900. Here the table 1900 is provided with one or more adjustable arms 1910 to which the connector 1840 is attached. In operation, the arms 1910 are adjusted to place the connector in the desired orientation in relation to the patient's spine. Instruments 1600a, 1600b may then be attached to the connector to maintain the vertebral bodies, to which the instruments 1600a, 1600b are attached, in proper alignment. The position of the connector 1840 may be further adjusted at needed to maintain proper alignment. Other possible connections and configurations will be apparent to one skilled in the art given the benefit of this disclosure.

While the instruments and methods disclosed herein have been particularly shown and described with reference to the example embodiments thereof, those of ordinary skill in the art will understand that various changes may be made in the form and details herein without departing from the spirit and scope of the present invention. Those of ordinary skill in the art will recognize or be able to ascertain many equivalents to the example embodiments described specifically herein by using no more than routine experimentation. Such equivalents are intended to be encompassed by the scope of the present invention and the appended claims.

What is claimed is:

1. An instrument for manipulating a vertebral body, the instrument comprising:
 a first arm having a proximal end and a distal end, the distal end configured to engage a removable attachment element of a first implant assembly implanted in a vertebral body, said distal end of said first arm creating a pin joint with the first implant assembly that facilitates derotation of the vertebral body; and
 a second arm pivotably connected to the first arm having a proximal end and a distal end, the distal end configured to engage a removable attachment element of a second implant assembly implanted bilaterally from the first implant assembly in the vertebral body,
 wherein the removable attachment element of the first implant assembly and the removable attachment element of the second implant assembly are configured to be removable from the first implant assembly and the second implant assembly implanted in the vertebral body, respectively; and
 wherein the removable attachment elements comprise one or more detachable tabs extending from at least one of the implant assemblies.

2. The instrument of claim 1, further comprising a handle disposed at the proximal end of at least one of the first or second arms.

3. The instrument of claim 1, wherein the distal ends of the first and second arms pivotably engage the removable attachment elements of the first and second implant assemblies.

4. The instrument of claim 3, wherein the distal ends of the first and second arms comprise feet for engaging through holes of the removable attachment elements of the first and second implant assemblies thereby forming the pin joint.

5. The instrument of claim 1, wherein the proximal end of at least one of the first or second arm further comprises a connection element configured to engage a connector for connecting the instrument to another instrument.

6. An implant assembly for use in bilateral vertebral body manipulation, the implant assembly comprising:
 a bone anchor having a proximal head and a distal shaft extending along a longitudinal axis configured to engage bone;
 a body configured to engage the proximal head of the bone anchor and engage a spinal fixation element;
 a removable attachment element extending from the body for connecting the implant assembly to an arm of an instrument configured to manipulate the implant assembly in a bilateral arrangement, wherein the removable attachment element is configured to be removable from the implant assembly implanted in the vertebral body; and
 wherein the removable attachment element comprises one or more tabs extending from the body that are detachable and wherein the one or more tabs include a thru-hole configured to engage a distal end of an instrument to create a pin joint facilitating derotation of the vertebral body.

7. The implant assembly of claim 6 wherein implant assembly is a polyaxial screw.

* * * * *